United States Patent [19]
Trampler et al.

[11] Patent Number: 5,626,767
[45] Date of Patent: May 6, 1997

[54] ACOUSTIC FILTER FOR SEPARATING AND RECYCLING SUSPENDED PARTICLES

[75] Inventors: Felix Trampler, Hinterbruehl, Austria; James M. Piret, Vancouver, Canada; Stefan A. Sonderhoff, Vancouver, Canada; Douglas G. Kilburn, Vancouver, Canada

[73] Assignee: SonoSep Biotech Inc., Richmond, Canada

[21] Appl. No.: 88,547

[22] Filed: Jul. 2, 1993

[51] Int. Cl.$^6$ .................................... C02F 1/36
[52] U.S. Cl. ........................... 210/748; 435/261
[58] Field of Search ................ 210/748, 198.1, 210/542; 435/173.1, 261

[56] References Cited

U.S. PATENT DOCUMENTS

| | | | |
|---|---|---|---|
| 4,055,491 | 10/1977 | Porath-Furedi | 210/748 |
| 4,523,682 | 6/1985 | Barmatz et al. | 209/638 |
| 4,673,512 | 6/1987 | Schram | 210/748 |
| 4,759,775 | 7/1988 | Peterson et al. | 55/15 |
| 4,877,516 | 10/1989 | Schram | 209/155 |
| 5,164,094 | 11/1992 | Stuckart | 210/708 |
| 5,225,089 | 7/1993 | Benes et al. | 210/748 |

FOREIGN PATENT DOCUMENTS

| | | |
|---|---|---|
| 821419 | 12/1937 | France . |
| 3027433A1 | 2/1982 | Germany . |
| 0147032 | 7/1985 | WIPO . |
| 0929470 | 11/1988 | WIPO . |
| WO88/09210 | 12/1988 | WIPO . |
| WO90/05008 | 5/1990 | WIPO . |

OTHER PUBLICATIONS

Curtis, H. W. and E. J. Stephans, "Ultrasonic Continuous Flow Plasmapheresis Separator," *IBM Technical Disclosure Bulletin*, IBM Corporation, Jun. 1982, vol. 25, No. 1.

Benes, E., et al., "Abscheidung Dispergierter Teilchen Durch Ultraschallinduzierte Koagulation," *Tagung der Deutschen Arbeitsgameinschaft fur Akustik—DAGA '89*, 1989.

(List continued on next page.)

*Primary Examiner*—Ivars Cintins
*Attorney, Agent, or Firm*—Seed and Berry LLP

[57] ABSTRACT

Particulate material suspended in a fluid is separated and recycled by means of an ultrasonic resonance wave. In a preferred embodiment, the ultrasonic resonance field is generated within a multilayered composite resonator system including a transducer, the suspension and a mirror parallel to each other. Dimensions and frequencies resonant to the whole system but not exciting Eigen-frequencies of transducer and mirror itself are chosen so that thermal dissipation is minimized. Criteria for flow direction and flow rate are defined in order to maintain a high-quality factor of the composite resonator and to achieve a high-separation efficiency. Generally, the process is suitable for all kinds of particles (solid, liquid or gaseous disperse phases) especially for hydrosols (particles in water) and for separation of biological particles such as mammalian, bacterial and plant cells or aggregates. Specialized applications in biotechnology are described including an acoustic filter for mammalian cell bioreactors or the selective retention of viable cells relative to non-viable cells.

27 Claims, 11 Drawing Sheets

OTHER PUBLICATIONS

Hager, F., and E. Benes, "A Summary of All Forces Acting on Spherical Particles in a Sound Field," *Proc. of the Ultrasonic International '91 Conference and Exhibition*, Le Touquet, France, Jul. 1991.

Apfel, R.E., "Acoustic Radiation Pressure—Principles and Application to Separation Science," *Fortschritte der Akustik—DAGA '90*, pp. 19–36, 1990.

Mandralis, Z.I., et al., "Transient Response of Fine Particle Suspensions to Mild Planar Ultrasonic Fields," *Fluid/Particle Sep. J.* 3(3):115–121, Sep. 1990.

Kilburn, D.G., et al., "Enhanced Sedimentation of Mammalian Cells Following Acoustic Aggregation," *Biotech. and Bioeng.* 34:559–562, 1989.

Groschl, M., and E. Benes, "Automatische Frequenzregelung fur Piezoelektrische Resonatoren und deren Implementierung im akustischen Driftwellenresonator," Diplomarbeit Institut fur Allgemeine Physik, Technischen Universitat Wien, Nov. 1991.

Nowotny, H., et al., "Layered Piezoelectric Resonators With an Arbitrary Number of Electrodes," *J. Acoust. Soc. Am.* 90(3):1238–1245, Sep. 1991.

Benes, E., "Improved Quartz Crystal Microbalance Technique," *J. Appl. Phys.* 58(3):608–626, Aug. 1981.

ACOUSTIC FILTER FOR SEPARATING AND RECYCLING SUSPENDED PARTICLES

TECHNICAL FIELD

The present invention is related to a method and apparatus for separating particles dispersed in a liquid. The present invention is particularly directed to a method and apparatus capable of continuously separating dispersed particles with acoustic properties that are different from the fluid. Generally, the process is suitable for all kinds of particles (solid, liquid or gaseous disperse phases) especially hydrosols (particles in water) as well for separation of biological particles such as mammalian, bacterial and plant cells or aggregates.

BACKGROUND OF THE INVENTION

Numerous fields of modem technology require that particles be removed from fluid. Such separation processes permit either the liquid phase or particulate matter to be recycled. In biotechnology, biological particles have to be removed from medium containing the product. Continuous stirred suspension bioreactors are operated with continuous addition of fresh medium and removal of spent medium, often containing the desired product. A number of systems have been developed to increase the cell density and productivity in these bioreactors by recycling cells from the spent medium stream. Of these systems, spin filters are most widely commercially available. Spinning (rotation) of these cylindrical filters inside bioreactors helps reduce the fouling of the filter surface. Nonetheless, the usefulness of these existing systems is limited by progressive protein and cellular fouling of the filters. Filter fouling and the build-up of nonviable cells in the suspended phase of spin-filter bioreactors generally limits the time of productive operation. The scale-up of spin-filters has been limited because, as the volume of bioreactors increases, it is not practical to provide enough filter area inside the reactor to maintain operation. Cross-flow, sedimentation and centrifugation systems are limited by fouling and sealability. They have not been widely used in industry. Centrifugation systems also have not been widely used, possibly because of the high cost.

Recently, great effort has been directed at the development of acoustic separation methods to replace or enhance conventional technologies. The establishment of a standing wave in the fluid results in the formation of velocity nodes or antinodes to which the particles are forced to migrate by the radiation force, depending on their compressibility and density. (Most solid and liquid particles move toward the velocity antinodes.) Nodes and antinodes are at right angles to the direction of propagation of the sound waves, and the nodes are spaced from adjacent nodes by a distance equal to one half of the wavelength of the acoustic wave. The aggregating effect of ultrasonic sound within these antinodes has already been described in the literature. From E. Skudrzyk, "Die Gnundlagen der Akustic," Springer Verlag, Wien, 1954, S. 202–205, S. 807–825; L. Bergmann, "Der Ultraschall und seine Anwendungen in Wissenschafi und Technik," Verlag hirzel, Zuerich, 1954: as well as K. Asai and N. Sasaki, "Treatment of slick by means of ultrasonics," Proceedings of the 3rd International Congress on Coal Preparation, Institut National de l'Industrie Charbonniere, Brussels-Liege, 1958, it follows that the frequency to be used in the applied sound is best chosen within the magnitude of the so-called characteristic frequency $f_0$, which can be calculated from $$f_0 = \frac{(3\eta)}{2\pi r^2} = \frac{0.48\eta}{r^2}, \quad (I)$$

whereby $\eta$ constitutes the kinematic viscosity and r the radius of the particle. Using this frequency range, the effect of radiation force and cumulative acoustically induced Bernoulli forces within the antinode planes can be maximized.

According to U.S. Pat. No. 4,055,491, ultrasonic standing waves are used to flocculate small particles, such as blood or algae cells, within the velocity antinodes of the acoustic field so that they settle out of the carrying liquid by gravity. But the undefined placement of the ultrasonic source and therefore low efficiency of the standing wave field due to undefined resonance boundary conditions result in high energy losses due to a considerable fraction of traveling waves. The described process is limited to discontinuous operations. The apparatus presented in U.S. Pat. No. 5,164,094 mainly modifies the geometry compared to the embodiments described in U.S. Pat. No. 4,055,491. However, a considerable portion of energy is still lost since frequencies of the sound field applied to the vessels carrying the dispersion is not controlled by well-defined resonance boundary conditions.

An embodiment to separate particles with various acoustic qualities is described in U.S. Pat. No. 4,523,682. A low resonance mode of a vessel containing a dispersion is excited by a relatively small transducer mounted at one end of the vessel, resulting in node and antinode planes perpendicular to the transducer/vessel interface. Perpendicular modes created by the acoustic point source mean that the system cannot be described as a one-dimensional resonator. The fraction of attenuated traveling waves in the longitudinal direction is high compared to the accumulated acoustic energy in the transversal standing wave field. Acoustic attenuation results in a temperature increase within the dispersion along the flow direction. Temperature changes affect sound velocity and resonance frequency, and cause a non-homogeneous temperature distribution along the flow direction which decreases the resonance quality of the field. As a result, the treatment period necessary to achieve the desired separation is prolonged.

Because of the long acoustic treatment periods necessary to achieve aggregation and sedimentation of the particles captured in the antinode planes, efforts were undertaken to move the antinodes of a standing wave relative to the dispersion, in order to obtain the desired separation effect directly by utilizing acoustic forces alone. U.S. Pat. No. 4,673,512 introduces an interference standing wave field generated by opposing transducers which are excited with the same frequency. By controlling the phase shift between the electric excitation signals of the two acoustic sources, it is possible to move particles trapped within the antinodes or nodes of the traveling interference pattern in the dispersion. Using this method, a relatively short treatment period can be achieved. The disadvantage of this method is its non-resonant nature. Much more energy is used to maintain an interference standing wave field compared to a resonant standing wave field of the same amplitude. The result is higher electrical power consumption and thermal dissipation for producing a given acoustic particle velocity amplitude. The same problem has to be considered in U.S. Pat. No. 4,759,775, in which only the method of creating the traveling interference pattern is different.

U.S. Pat. No. 4,877,516 introduces the idea of the controlled movement of local gradients of the acoustic amplitude of the standing field perpendicular to the direction of sound propagation. Thus, particles are moved within the antinodes or nodes of the field by the Bernoulli-force which is directly related to described gradients and is acting parallel to the antinode planes. The disadvantage of the embodiment is the requirement of mechanically moving array to produce acoustic shadows in order to achieve the desired movement of local gradients of the standing wave.

Stepwise movement of the antinodes of a resonant standing wave by exciting succeeding resonance modes of the resonator system is described in the PCT Appl. No. PCT/AT89/00098. Although resonance boundary conditions are fulfilled in some of the described embodiments, there is still considerably acoustically induced dissipation due to the resonator frequencies used, which have always been chosen very close to an Eigen-frequency of the transducer in the past.

SUMMARY OF THE INVENTION

According to principles of the present invention, an ultrasonic resonance field is generated within a multilayered composite resonator system which includes a transducer, the suspension and a mirror. The suspension consists of a liquid containing particles to be separated. Acoustic radiation force moves the particles in the liquid towards the nodes or antinodes of the standing wave. Secondary lateral acoustic forces cause them to aggregate and the aggregates settle by gravity out of the liquid.

The flow rate of the liquid is selected to ensure that the liquid does not undergo a significant temperature change within the resonator system. According to principles of the present invention, the temperature change of the liquid shall not cause a phase shift of greater than $\pi/2$ within the resonator system.

In biotechnology, cells are used to produce proteins of pharmaceutical importance. Most of these proteins require a further step in protein synthesis called post-translational modification. Mammalian cells rather than bacteria are used to produce these proteins because only they can achieve such complicated modifications. The protein products of most mammalian cells are secreted into the medium. For batch bioreactors, cells have to be separated from the medium after a rim. For continuous flow reactors, cells can be recycled back to the bioreactor to increase productivity. Ultrasonically induced aggregation and sedimentation is applicable to both continuous flow suspension bioreactors and downstream processing. The mammalian cells are thus separated from the liquid culture in which they are grown and kept in the bioreactor while permitting harvesting of the protein from the liquid.

To avoid any misunderstanding in the comparison of the prior art with the object of the invention, the following definitions are presented to clarify their use strictly throughout this description.

"Acoustic particles" are simply the volume elements of the acoustic continuum theory and must not be confused with the suspended particles. The "acoustic particle velocity" is the time derivative of the periodic acoustic particle displacement caused by the regarded sound wave.

"One-dimensional" treatment of composite resonators means, that an approximate model is applied, where all quantities are regarded as being exclusively dependent from only one direction (compare, e.g., H. Nowotny, E. Benes, and M. Schmid, *J. Acoust. Soc. Am.* 90(3), September 1991). This direction is coinciding throughout this description with the longitudinal direction.

The term "layer" is very generally used. Even the liquid carrying the suspended particles is regarded as a layer. This essential resonance frequency-determining dimension is usually, but not necessarily, the thickness dimension of the layer. The x-axis of the coordinates is chosen in the direction of this layer dimension, perpendicular to the flow direction. The y-axis direction is the depth of the layer and is perpendicular to the x-axis direction and to the flow direction. The z-axis direction is parallel to the fluid flow direction.

"Active layers" consist of piezoelectric material, "passive layers" consists of non-piezoelectric material.

"Transducer" is in the most simply case a single layer of a piezoelectric material. For many reasons it is advantageous to bond several piezoelectric plates with one or on both sides upon passive, electrically insulating carrier layers. According to the invention, additional transformation (sub)layers may be used. The transducer-layer itself consists in the most general case of a number of solid layers, whereby the piezoelectric layer is contained and the outermost layers are in contact with the surrounding air or the dispersion layer(s), respectively.

"Phase shift $\phi$" is the spatial phase shift of the acoustic particle velocity V:

$$\phi = 2\pi \cdot f_e \frac{x}{v} \qquad (II)$$

where $f_e$ is the electrical driving frequency, x is the resonance determining dimension of the regarded layer, and v is the sound (phase) velocity of the regarded layer. The total phase shift of a multilayer is the sum of the phase shifts of each layer and the additional phase jumps at the interface planes between adjacent layers with different specific acoustic impedances. The delta phase shift $\Delta\phi$ refers to the phase shift changes of the standing wave over its entire length in the acoustic resonation chamber containing the fluid. A change of 180° is a phase shift of $\pi$, a change of one full wave is a phase shift of $2\pi$, whereas a change of 90° and 45° is a phase shift change of $\pi/2$ and $\pi/4$, respectively.

"Harmonic Eigen-frequencies" or the harmonic resonance frequencies, $f_i$, of a single layer are defined by $$f_i = \frac{i \cdot \left(\frac{c}{p}\right)^{1/2}}{2 \cdot x} \qquad (III)$$

where i is the number of the regarded harmonic frequency, x is the resonance determining dimension, c is the effective elastic constant, and p is the mass-density of the layer.

If the layer is consisting of a piezoelectric material, the effective elastic constant c in equation (III) depends upon the electrical load between the electrodes. For the limit cases of short-circuited and open-loop electrodes, the so-called series or parallel Eigen-frequencies are determined, respectively. Only an odd subset of the Eigen-frequencies $f_i$ can be electrically excited.

"Quasi-harmonic Eigen-frequencies" of a multilayer (e.g., a multilayered transducer). While the overtone frequencies of a single homogeneous layer are integer multiples of the fundamental Eigen-frequency, the overtone-frequencies of a composite resonator are in general not that trivially spaced. For that reason, the Eigen-frequencies of a one-dimensional composite resonator are sometimes called "quasi-harmonic resonance frequencies." (Compare, e.g., E. Benes, *J. Appl. Phys.* 56(3), Aug. 1, 1984). However, in the case of one layer with dominating dimension (dispersion layer), in a first approximation also the high overtone composite frequencies may be regarded as equidistant. Since a transducer according to the invention usually consists of more than one single layer, it is a multilayered resonator itself. For such a resonator, the Eigen-frequencies can be defined as the frequencies for which the phase shift $\phi_T$ of the acoustic particle velocity amplitude along the dimension $x_T$ of the transducer between the outermost planes is equal to an integer multiple n of the number $\pi$. Not all of these mechanically possible resonance frequencies are piezoelectrically excitable. The excitability depends on the displacement curve along the active layer alone. If this curve is a symmetric one, the transducer is not excitable at the corresponding frequency. This definition of the electrically excitable Eigen-frequencies of a multilayered transducer corresponds with the measurable resonance frequencies, if the transducer is surrounded by vacuum (or air) and the frequency of the driving electrical power generator is tuned to the relative maxim of the electrical active power consumed by the resonator. If the voltage amplitude $U_e$ of the driving power generator is kept constant (very low electrical source impedance), the so-called series resonance frequency of the composite structure is determined. If the current amplitude $I_e$ of the driving power generator is kept constant (very high electrical source impedance), the so-called parallel resonance frequency of the composite structure is determined.

"Longitudinal direction" means the direction of the layer thickness dimension. The longitudinal direction coincides with the propagation direction of the sound wave excited by the transducer layer. According to the present invention, resonance modes of the composite resonator are excited in longitudinal direction. Therefore, the direction of the standing resonance wave is referred to as the longitudinal direction.

"Resonance frequencies $f_C$ of the multilayered composite resonator" result from the condition for longitudinal resonance, whereas the total phase shift $\phi_C$ of the acoustic standing wave across the total length of a composite resonance system, including all layers, has to be an integer multiple of the number $\pi$. This definition of the resonance frequencies of the composite resonator corresponds with the measurable resonance frequencies if the frequency of the driving electrical power generator is tuned to the relative maxim of the electrical active (root mean square) power consumed by the resonator.

"Eigen-frequencies $f_T$ of the transducer" result from the condition that the phase shift $\phi_C$ between the terminating planes of the transducer layer has to be an integer multiple m of the number $\pi$. This definition of the Eigen-frequencies of a transducer corresponds with the measurable resonance frequencies, if the transducer is surrounded by vacuum (or air) and the frequency of the driving electrical power generator is tuned to the relative maxim of the electrical active power consumed by the resonator. Generally, the transducer may consist of several layers. If the transducer is formed by a single piezoelectric layer covered with electrodes, the condition for Eigen-frequencies is given by $$\phi_T = 2\pi \cdot x_T \cdot f_{T,m}/v_T(q,m) = m \cdot \pi, \qquad (IV)$$

whereby m is the number of the regarded Eigen-frequency $f_{T,m}$; $x_T$ is the resonance determining thickness; and $v_T$ is the longitudinal sound velocity of the transducer, which is depending on the electrical charge q at the electrodes and the number m of the regarded Eigen-frequency.

"Eigen-frequencies $f_M$ of the mirror" result from the condition that the phase shift $\phi_M$ between the surfaces of the reflector layer has to be an integer multiple n of the number $\pi$. If the mirror is formed by a single layer only, the condition for Eigen-frequencies is given by $$\phi_M = 2\pi \cdot x_M \cdot f_{M,n}/v_M = n \cdot \pi, \qquad (V)$$

whereby n is the number of the regarded harmonic Eigen-frequency $f_{M,n}$, $x_M$ is the resonance determining thickness, and $v_M$ the longitudinal sound velocity of the mirror.

"Transversal directions" are directions perpendicular to the longitudinal direction. These directions fall in the particle velocity node and antinode planes of the standing resonance wave.

"Specific acoustic impedance Z" is the acoustic impedance per cross-sectional area of the regarded material.

The present invention is directed to a method and apparatus capable of continuously separating and recycling dispersed particles with acoustic properties (compressibility, sound velocity) different than the suspension medium. The methods of the present invention use acoustically induced forces to retain and aggregate dispersed particles and gravity to settle and recycle the aggregates. According to the preferred embodiments, an acoustic resonance wave inducing said forces is excited within a multilayered composite resonator system. The multilayered resonator consists at least of a transducer layer, an acoustic mirror layer and the suspension layer in between. All acoustically coupled layers are parallel to each other. The invention is suitable to separate dispersed particles, with sizes ranging from $10^{-3}$ to 1 min. Preferred resonance frequencies according to acoustic and geometric properties of the particles range from 0.1 to 10 MHz.

The invention provides an ultrasonic resonance field between transducer and a mirror of a multilayered composite acoustic resonator, capable of separating and recycling particles from fluid, while minimizing the effect of any temperature increase caused by acoustically induced dissipation. Many potential applications for ultrasonic separation processes (for example in biotechnology) require a separation method where temperature increases are minimized in order to avoid thermal damage to the particles. Furthermore, the accumulated energy of the established acoustic resonant field and therefore the acoustic treatment time necessary to achieve separation depends on a homogeneous temperature distribution along flow direction perpendicular to direction of sound propagation. Because the wavelength of an acoustic wave is partially dependent on temperature, an undesired spatial temperature gradient along flow direction perpendicular to the longitudinal direction of the standing wave results in a non-homogeneous distribution (in flow direction) of the total phase shift of the acoustic wave between the terminating planes of the composite resonator. Constant phase shift distribution in transversal directions is a boundary condition for maintaining high quality resonance fields. Therefore, thermal dissipation has to be minimized and flow velocity of the suspension optimized.

With standard transducers, heat is generated by the transducer, causing the fluid to increase in temperature. Even if this transducer heating is minimized by various techniques, such as circulating a flow of a coolant around the transducer as shown in FIG. 8, or use of the optimized transducer and mirror design as shown in FIGS. 1–7 and described in detail herein, there is still an induced thermal dissipation due to acoustic attenuation within the suspension layer itself. This thermal heating, in combination with the flow of the liquid, causes a temperature increase in the liquid in the flow direction. Generally, sound velocity $v_S$ within the suspension is depending on temperature T of the suspension. Thus, the phase shift $\phi_S$ of the acoustic wave between transducer and mirror varies with temperature, too:

$$\phi_S(T) = 2\pi \cdot x_S \cdot f_c/v_S(T), \qquad (VI)$$

According to the invention, the flow is defined as perpendicular to the direction x of the acoustic wave and parallel to the direction z. A temperature distribution $T_S(z)$ in direction z, averaged in direction x, causes a non-homogeneous distribution $\phi_S(z)$ of spatial phase shift of the acoustic wave within the suspension layer. This relationship is, in first approximation, best described by $$\Delta\phi_S = \phi_S(T) \cdot \alpha(T) \cdot \Delta T \qquad \text{(VII)}$$

and results from the equation (VI). The coefficient $\alpha = -(1/v_S) \cdot (\partial v_S/\partial_T)$ describes the dependency of sound velocity $v_S$ on temperature T and can be determined experimentally. The temperature range $\Delta_T$ within the resonator can be calculated from inflow temperature minus outflow temperature. The resulting range of phase shift $\Delta\phi_S$ prevents a high quality factor $Q_S$ of the suspension layer, which can only be achieved if the phase shift $\phi_S$ is constant in transversal direction z. $Q_S$ is defined by $$Q_S = 2\pi \cdot E_S/W_S, \qquad \text{(VIII)}$$

whereby the accumulated acoustic energy $E_S$ of the resonance field within the suspension is responsible for acoustic forces acting on the dispersed particles and causing them to aggregate. $W_S$ indicates the portion of acoustic energy attenuated by the suspension within the time period $1/f_C$. This attenuation is responsible for thermal dissipation within the suspension.

As a result, temperature gradients in flow direction z perpendicular to direction x of the standing wave lower the quality factor $Q_S$ and thus, lower the accumulated acoustic energy $E_S$ of the resonance field within the fluid. Decrease of the accumulated acoustic energy $E_S$ may suggest that prolonged treatment time is necessary to achieve acoustically induced aggregation and separation of the particles. If one decides to lower the flow velocity to prolong treatment time this results in an even larger temperature gradient along flow direction. Ultimately, quality factor $Q_S$ vanishes and the resonance field collapses completely at too low flow rates.

The present invention avoids the lower of the quality factor $Q_S$ by setting a lower limit of flow velocity, according to the present invention. The lower limit flow velocity is selected to be of a value, which results in a phase shift distribution $\phi_S(z)$ within the suspension layer having a total range $\Delta\phi_S$ of less than one half of $\pi$. Generally, if only prior art techniques are used, there is a possibility that this flow criterion may result in a retention time of the suspension inside the acoustic resonance field too short to aggregate particles sufficiently to allow sedimentation. According to one embodiment of the present invention the flow direction is oriented against the force of gravity. As soon as acoustically induced aggregation occurs, gravity becomes a dominant force and compensates for Stokes drag force (which is responsible for moving the dispersed particles within the fluid in flow direction) and causes the particles to not be advanced by the liquid. Due to acoustically induced Bernoulli forces acting in transversal directions to the direction of the standing wave, particles are trapped within the antinode planes of the resonance field as the liquid passes through the composite resonator. This results in considerably higher effective retention times of suspended particles inside the resonance field compared to the retention time of the fluid. Furthermore, particle concentration of the suspension is increased within the acoustic resonance field enhancing aggregation. Once the aggregates become large enough to overcome the fluid drag and acoustically induced Bernoulli forces, they settle out of the liquid under the force of gravity, against the flow.

The inflow pipe of the resonator is, preferably, also the settling tube with inner dimensions limited by the preferably square shaped (x,y) cross section of the suspension layer to keep flow velocity within the settling tube low. Maximizing the inflow/settling tube diameter minimizes the flow velocity within the tube.

According to one embodiment of the present invention, turbulence inside the settling tube is minimized by at least two sets of baffles. The (x,y) cross section (perpendicular to flow direction z) of such a set is grid shaped. The relatively low grid frequency ranging between 1.5 to 5 $cm^{-1}$ avoids breaking up settling aggregates. A multiple of sets of baffles placed inside the tube prevents turbulence more effectively than a single set of multiple length. If required, a single pass shell and tube heat exchanger could replace one set of baffles to precool fluid before entering the resonator.

In addition, the invention presents another alternative approach to overcome the decrease of resonance quality caused by temperature gradients along flow direction. The suspension layer is divided into at least two sections by an acoustically transparent layer perpendicular to the direction x of the standing wave and referred to as film layer. The liquid flows through adjacent sections $S_i$ essentially in opposite flow orientation z, −z, with flow velocities resulting in temperature distributions $T_i(z)$ in the regarded section $S_i$. The temperature distributions $T_i(z)$ result in a temperature distribution T(z) in direction z, averaged in direction x across all suspension sections $S_i$. This temperature distribution T(z) causes the non-homogeneous distribution $\phi_S(z)$ of spatial phase shift of the acoustic wave within the suspension to be within a total range $\Delta\phi_S$ of less than one half of $\pi$. Therefore, the effects of temperature gradients in flow direction caused by acoustically induced dissipation are compensated for by counter flow.

Furthermore, according to another alternative embodiment of the invention, the piezoelectrically active layer of the transducer can be formed by at least two adjacent piezoelectric plates and, thus, be divided into at least two independent segments. Each transducer segment can be described as an independent transducer and excited by an individual electrical power generator. The non-homogeneous temperature distribution T(z) as described above causes individual resonance frequencies of each of the standing waves within the resonator created by the two separate transducers. Using two or more transducers has the advantage that the flow velocity criterion does not have to be fulfilled for the entire flow path of the suspension within the resonator, but only within each regarded segment of the resonator associated with each transducer, respectively. Furthermore, individual periods of excitation of the piezoelectric transducers can be interrupted by periods of no excitation of one of them to allow controlled settling of aggregates within the regarded segments of the resonator. When the acoustic resonance field of one segment is switched off, the remaining resonance fields of adjacent segments remain on and prevent remixing.

A variation of the present invention is the so-called two-dimensional resonator system, possibly acting as an additional step to the described one-dimensional resonator system to separate low particle concentrations from a liquid. The two directions of a two-dimensional resonance field are preferably perpendicular to each other. Perpendicular acoustic radiation forces result in the migration of suspended particles towards the intersection lines of the antinode planes of each of the two one-dimensional resonance fields. Higher particle concentrations can be achieved at these intersection lines than within a single antinode plane. To achieve acoustically induced aggregation, a minimum particle concentration is required. Therefore, the higher particle concentration at the antinode lines of a two-dimensional field result in a lower supernatant particle concentration within the liquid at the outflow.

Since the frequencies $f_C$ of the resonance modes of the composite system vary with temperature of the fluid and its particle concentration, it is necessary to compensate the exciting frequency $f_e$ for resonance frequency drifts. This can be achieved by controlling the fine tuning of the exciting frequency $f_e$ by an automatic frequency control (AFC) which utilizes a relative maximum of the active electrical power consumption $P_{el}$ of the composite resonator as criterion for resonance. Another approach to control the exciting frequency $f_e$ towards a preferred resonance frequency $f_C$ is to maximize the acoustically induced electrical signal in a piezoelectrically active layer (e.g., PZT ceramics, Lithium-Niobate monocrystals, or PVDF layers) used as mirror or included in a composite mirror.

One application of the present invention is its use in the separation from nutrient medium and recycling of cultured mammalian cells grown in a perfused stirred tank bioreactor chamber. Retention of cells within the bioreactor chamber and the ability to continuously replenish nutrient medium allows growth to occur up to high cell densities. The settling tube, which also may be the inflow tube, is directly connected to the bioreactor chamber. The pump is preferentially placed after the outlet side of the resonator chamber to avoid mechanically damaging the recycled cells. The maximum acoustic particle velocity amplitude within the suspension is also maintained at a value that will not result in damage to the cells. The preferred resonance frequency $f_C$ of the composite resonator ranges between 2 to 4 MHz. If required, the flow velocity of the suspension can be tuned to result in a significantly higher separation efficiency for viable cells than for non-viable cells. This effect is due to the different diameters and compressibilities of viable and non-viable cells, which results in weaker acoustic forces acting on non-viable cells compared to viable cells. The selective concentration of viable cells results in increased culture viability, a major advantage over existing cell recycling technologies which tend to accumulate non-viable cells within the bioreactor chamber. For the purposes of this example, separation efficiency is hereby defined as the ratio of the number of cells being separated from the liquid by acoustically induced aggregation and sedimentation to the number of cells entering the resonator within the same period of time. Viability is hereby defined as the ratio of viable cells to the total number of cells. Materials facing the cell suspension are compatible with cultured cells. These materials include: stainless steel, Teflon, borosilicate glass or various ceramics (e.g., alumina). Glass and ceramics can be used to form the piezoelectric passive layer of the transducer and the mirror.

The embodiment in which the resonation chamber is designed such that the resonant frequency for the resonator chamber is different from the Eigen-frequencies of the transducer and mirror has been briefly described. These features will now be summarized in greater detail. However, the present invention does not require that such a mismatched transducer and resonation chamber be used. The present invention, as claimed herein, can be used with numerous transducer and resonation chamber configurations and is not restricted to this preferred embodiment as described herein. Thus, prior art transducers can be used with the present invention. The invention of this application is defined by the appended claims and is not limited to just the preferred embodiments of transducer designs described herein.

A patent application has been filed in Austria on May 11, 1993 bearing Application Number A 926/93 that describes and claims the alternative embodiments which are summarized in the next section. The U.S. patent application claiming priority from this Austrian patent application is filed concurrently herewith and bears U.S. application Ser. No. 08/086,700, filed on Jul. 2, 1993 and names as inventors Felix Trampler, Ewald Benes, Wolfgang Burger, and Martin Gröschl. This related application has one common inventor, Felix Trampler, to the present U.S. application, as filed, and claims related subject matter. So that one possible transducer and resonation chamber design can be clearly understood, the subject matter of the related Austrian priority application and concurrently filed U.S. application will now be summarized, and then described in the text, in detail.

According to one of the preferred embodiments, the multilayered composite resonator system consists of a plane transducer, a vessel containing the dispersion and a plane acoustic mirror. All acoustically coupled layers are arranged in longitudinal direction and their surfaces are parallel to each other. The transducer may consist of a piezoelectrically active layer, such as PZT (Lead-Zirconate-Titanate) ceramics or Lithium-Niobate monocrystals or PVDF layers, and a solid passive layer acting as carrier of the active layer. The invention is suitable to separate dispersed particle sizes ranging from $10^{-3}$ to 1 mm. Preferred resonance frequencies according to acoustic and geometric properties of the particles range from 0.1 to 10 MHz.

The first alternative embodiment of a first feature will now be summarized. According to principles of a first embodiment of one feature of the present invention, acoustically induced thermal dissipation of transducer and mirror within a composite resonator system are minimized by only exciting longitudinal acoustic resonance frequencies $f_C$ of the multilayered composite resonator, which are not in the range of any of the Eigen-frequencies $f_T$ of the transducer or $f_M$ of the mirror. Generally, the electrical excitability of a transducer at one of its Eigen-frequencies is much higher than its electrical excitability between adjacent Eigen-frequencies. As a result, in the prior art, a transducer has always been excited close to one of its Eigen-frequencies to generate a standing wave within the suspension. This has resulted in considerable thermal dissipation of the transducer in the prior art.

According to one first feature of the invention, avoiding excitation of any of the Eigen-frequencies of the transducer layer or mirror layer is helpful for choosing the layer-thicknesses and the frequency $f_e$ of the electrical signal exciting the transducer. Lower electrical excitability of the transducer at such excitation frequencies is of less importance, if resonance conditions within the multilayered resonator are maintained. Resonance frequencies $f_C$ of the composite resonator result from the condition for longitudinal resonance, whereas the total phase shift $\phi_C$ of the acoustic standing wave across the total length of a composite resonance system, including all layers, has to be an integer multiple of the number $\pi$.

As a result of the present invention, the loss characterizing figure $R=W_e/E_S=P_e \cdot \tau C_j/E_S$ is minimized. The loss figure R is defined as the ratio between the active electrical energy consumption $W_e$ (per period $\tau C_{cj}=1/f_{Cj}$) of the composite resonator system and the reactive accumulated acoustic energy $E_S$ of the resonance field in the fluid; $f_{Cj}$ is the excited quasi-harmonic resonance frequency of the composite resonator. $P_e$ describes the active (root mean square) electrical power input, $$P_e = \tfrac{1}{2} U_e I_e \cos\phi, \tag{IX}$$

whereby $U_e$, $I_e$ are the amplitudes of the driving voltage and current, respectively, $\phi$ is the phase between both.

The accumulated acoustic energy $E_S$ is directly related to the acoustic forces acting on the particles, whereby the energy consumption $W_e$ compensates for attenuation of the acoustic field causing thermal dissipation. A small portion of $W_e$ also represents dielectric losses of the transducer, which are of no relevance to the present invention and will not be mentioned further.

Acoustically induced thermal dissipation of transducer and mirror can be minimized by exciting an acoustic quasi-harmonic composite resonance frequency $f_{Cj}$ of the total resonator, but simultaneously mismatching the driving frequency $f_e$ with any of the quasi-harmonic Eigen-frequencies $f_{Ti}$ of the transducer as well as with any of the Eigen-frequencies $f_{Mk}$ of the mirror. As a consequence, the characterizing loss figure R is significantly reduced. This mismatching between driving frequency and Eigen-frequency of the transducer is not at least obvious, since in the mismatched case the composite resonator shows a rather poor electrical behavior. For example, in the locus of electrical admittance curves, the composite resonances, which are represented by circles, are much less recognizable. The resonance circles appear to be much smaller and are offset from the real axis. Because of these properties, in the general case it is much more difficult to design an electrical driving electronics for maintaining a resonance excitation offside a transducer Eigen-frequency. For that reason, in the prior art systems the excitation of a composite resonator has been performed always close to the fundamental or third quasi-harmonic Eigen-frequency of the transducer.

Composite resonance frequencies $f_{Cj}$ result from the boundary condition at the terminating, total reflecting surfaces of a composite resonator for a standing wave, whereas the maximum of the acoustic particle velocity amplitude has to coincide with the terminating planes. Therefore, the total phase shift $\phi_C$ across the total length $x_C$ of a multilayered composite resonance system in longitudinal direction, including all layers, has to be an integer multiple of the number $\pi$. Mismatching between the electrical driving frequency $f_e$ and the Eigen-frequencies $f_{Ti}$ of the transducer layer can be obtained for a given driving frequency either by proper choosing the transducer thickness $x_T$ and its relative position within the multilayered resonator, or by directly choosing the driving frequency equal to a composite resonance frequency which is sufficiently off-set from any excitable Eigen-frequency of the transducer.

According to one embodiment of the invention, the offset is sufficient, if it is chosen higher than a certain minimum offset. The minimum offset is equal to 10% divided by the quasi-harmonic number i of the regarded Eigen-frequencies $f_{Ti}$ of the transducer:

$$0 < f_e < [0.9 f_{T1}]; \ [1.1 f_{T1}] < f_e < [(1-0.\tfrac{1}{2}) f_{T2}]; \ [(1+0.\tfrac{1}{2}) f_{T2}] < f_e < [(1-0.\tfrac{1}{3}) f_{T3}]; \ [(0+0.\tfrac{1}{3}) f_{T3}] < f_e < [(1-0.\tfrac{1}{4}) f_{T4}]; \ [(1+0.\tfrac{1}{4}) f_{T4}] < f_e < . \quad (X)$$

By introducing this mismatching, the coincidence of the maxim of the acoustic particle velocity amplitude with both outermost transducer planes is avoided. The characterizing loss figure R is optimized, if the thickness $x_T$ and relative position of the transducer layer being chosen with regard to the driving frequency $f_e$ in such a way that a vanishing acoustic particle velocity amplitude V in the interface plane between transducer and the dispersion is obtained. In this preferred case, the mismatching between the driving frequency $f_e$ and all the excitable Eigen-frequencies $f_{Ti}$ of the transducer is maximal and the driving frequency $f_e$ is approximately in the middle of one of the allowed intervals defined in equation (X).

Thus, in a preferred embodiment, in order to avoid excitation of any of the Eigen-frequencies of the transducer, the thickness $x_T$ of the transducer is of a value, which causes a spatial phase shift $\phi_T$ of the acoustic particle velocity amplitude of the generated acoustic wave close to, or equal to, an odd multiple of the number $\pi/2$. In other words, the exciting frequency $f_e$ of the power generator driving the transducer is tuned toward such a high-overtone resonance frequency of the composite resonator $f_C$, which is close to the average of two adjacent Eigen-frequencies $f_{T,m}$, $f_{T,m+1}$ of the transducer:

$$f_C \cong (f_{T,m} + f_{T,m+1})/2 \quad (XI)$$

The transducer may consist of a piezoelectric layer, referred to as active layer, such as PZT (Lead-Zirconate-Titanate) ceramics, Lithium-Niobate monocrystals, or PVDF layers, and a solid non-piezoelectric layer, referred to as passive layer, acting as a carrier of the active layer. The carrier material has a specific acoustic impedance $Z_B$ in the range of the acoustic impedance of the piezoelectrically active layer $Z_A$.

Similar rules are valid for the mirror layer. The thickness $x_M$ of the mirror layer has to be properly chosen in order to avoid excitation of its Eigen-frequencies $f_{Mi}$. The relative position of the mirror layer, however, is fixed as the terminating reflecting layer of the multilayered resonator. Generally, the mirror may also consist of several layers.

The mirror consists of a material with a specific acoustic impedance $Z_M$ which is high compared to the specific acoustic impedance $Z_S$ of the suspension. Similar to the transducer, the thickness $x_M$ of the mirror is chosen to be of a value which causes a spatial phase shift $\phi_M$ of the acoustic particle velocity amplitude close to, or equal to, an odd multiple of the number $\pi/2$. In other words, the exciting frequency $f_e$ is tuned towards such a high-overtone resonance frequency of the composite resonator $f_C$, which is close to the average of two adjacent Eigen-frequencies $f_{M,n}$, $f_{M,n+1}$ of the mirror:

$$f_C \cong (f_{M,n} + f_{M,n+1})/2 \quad (XII)$$

whereby $x_S$ is the thickness of the suspension layer and $f_e$ the exciting frequency.

The transducer layer may form a terminating layer of the composite resonator. Furthermore, the transducer layer may consist of a piezoelectrically active layer, such as PZT (Lead-Zirconate-Titanate, $Pb(Ti,Zr)O_3$) ceramics, or Lithium-Niobate ($LiNbO_3$) monocrystals, or PVDF (Polyvinylidene Fluoride) polymers, and a solid passive layer acting as a carrier of the active layer with defined thickness to achieve low acoustically induced thermal dissipation. Best results can be achieved by using a carrier material with low acoustic attenuation and with a specific acoustic impedance $Z_B$ in the range of or higher than the specific acoustic impedance $Z_A$ of the piezoelectrically active layer. The thickness $x_A$ of the active layer is preferably of a value which causes a phase shift $\phi_A$ close to or equal to an odd multiple m of the number $\pi$. The thickness of the passive layer $x_B$ is preferably of a value which causes a phase shift $\phi_B$ being close to or equal to an odd multiple of half of the number $\pi$. Using these criteria, the acoustic particle velocity amplitude at the transducer/liquid interface approaches zero and the boundary condition for exciting an Eigen-frequency $f_{Ti}$ of the transducer is optimally avoided. As a result, energy dissipation of the transducer is minimized. Besides that, for this preferred arrangement, there is no decrease of excitability compared to the case of matching the driving frequency and one of the Eigen-frequency of a transducer.

The transducer layer can also be positioned between two dispersion layers. In that case, the thickness $x_A$ of the active layer is preferably of a value which causes a phase shift $\phi_A$ close to or equal to an odd multiple m of the number $\pi$. The thicknesses of the passive layers $x_B$, $x'_B$ (if any) on each side of the transducer are preferably of values which cause phase shifts $\phi_B$ $\phi'_B$ being close to or equal to an odd multiple n, n' of half of the number $\pi$, respectively. Furthermore, the thicknesses of the dispersion layers $x_S$, $x'_S$ and mirror layers $x_M$, $x'_M$ on each side of the transducer have to be chosen, so that the acoustic particle velocity amplitude at both transducer/liquid interfaces approaches zero and the boundary condition for exciting an Eigen-frequency $f_{Ti}$ of the transducer is maximally avoided. As a result, the energy dissipation of the transducer is minimized. Preferably, the thicknesses $x_B$, $x'_B$ of the passive layers, are equal and the layers are made of the same material.

An odd multiple q of passive sublayers, each of a thickness $x_{B,k}$ (k=1 ... q) causing a phase shift $\phi_{B,k}$ as described above for the thickness $x_B$ of a single passive layer, with alternating high (in the range of the active layer) and low (in the range of the dispersion) acoustic impedance, but starting and ending with high ones, is useful to further reduce energy dissipation when this ensemble of sublayers is arranged between the active layer and dispersion. Alternatively, low-impedance sublayers can also be formed by a liquid with low acoustic attenuation, optionally circulating in order to control temperature.

Since the frequencies $f_{Cj}$ of the resonance modes of the composite system vary with temperature of the fluid and particle concentration it is of significance to compensate the exciting frequency $f_e$ for resonance frequency drifts in order to maintain constant conditions according to the aim of the invention. This can be achieved by controlling the fine tuning of the exciting frequency $f_e$ by an automatic frequency control (AFC) which maintains the active electrical power consumption $P_e$ of the composite resonator at a relative maximum as criterion for resonance.

Another approach to control the exciting frequency $f_e$ towards a preferred resonance frequency $f_{Cj}$ is to provide an additional active layer (e.g., PZT ceramics, Lithium-Niobate monocrystals, or PVDF layers) as mirror or as part of a composite mirror and to utilize the amplitude of the acoustically induced electrical signal at the electrodes of this said active layer as control criterion for maintaining the excitation of the chosen composite resonance frequency $f_{Cj}$.

Similar to the thicknesses of the layers of a composite transducer, the thicknesses of the piezoelectrically active and passive layers of a composite mirror are advantageously chosen so that the acoustic particle velocity amplitude at the mirror/liquid interface approaches zero and the boundary condition for exciting an Eigen-frequency $f_{Ti}$ of the transducer is optimally avoided. As a result, we have found that energy dissipation of the mirror is minimized for a given acoustic particle velocity amplitude in the fluid.

Analogous to the sublayers of a transducer as described above, sublayers can be introduced in a composite mirror layer. An odd multiple q of passive sublayers of a composite mirror, each of a thickness $x_{B,k}$ (k=1 ... q) causing phase shifts $\phi_{B,k}$ as described above for a transducer, arranged between active layer of the mirror (if any) and fluid layer, with alternating high (in the range of the active layer) and low (in the range of the dispersion) acoustic impedance, but starting and ending with high ones, can be used according to the invention to further lower energy dissipation.

DETAILED DESCRIPTION OF THE INVENTION

In order to emphasize the basic features of the embodiments, the layers are labeled with alpha-characters, while all other parts are labeled with numbers. The embodiment of FIGS. 1–7 describe the transducer according to one preferred embodiment as claimed in the concurrently filed U.S. application bearing Ser. No. 08/086,700, filed on Jul. 2, 1993, by inventors Felix Trampler, Ewald Benes, Wolfgang Burger, and Martin Gröschl, as previously described.

Figure 1:
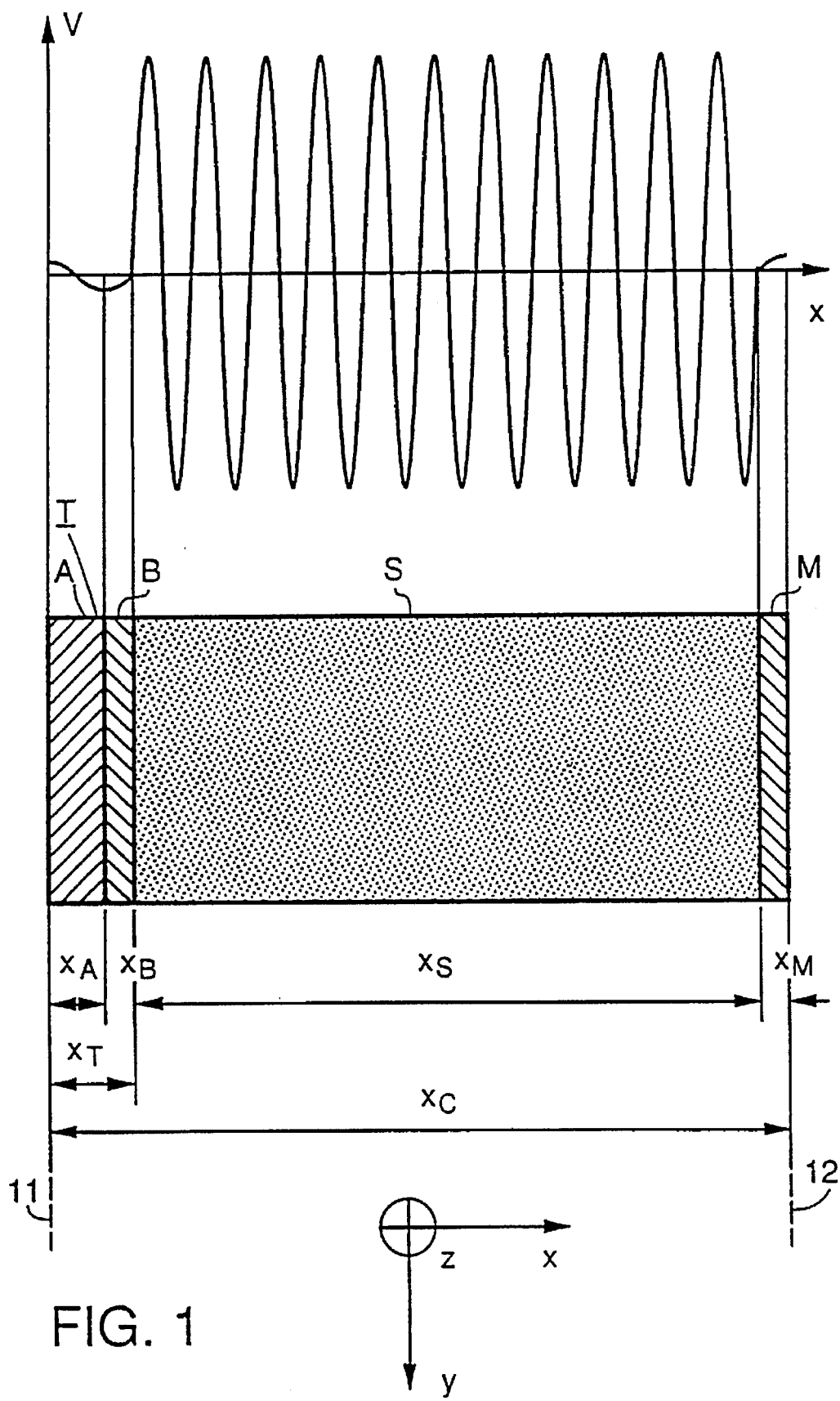
FIG. 1 shows the cross-sectional schematic view of the composite resonator as multilayered one-dimensional structure and the course of the resulting acoustic particle velocity amplitude, if the layer dimensions are chosen according to the invention.

The section of FIG. 1 shows a schematic of the basics parts and dimensions of a typical piezoelectric composite one-dimensional resonator. The transducer layer T on the left side preferably consists of an active piezoelectric layer A and a passive, electrically isolating, carrier layer B. The corresponding layer dimensions are $x_T$, $x_A$, and $x_B$, respectively. The transducer is acoustically coupled with the dispersion S; the dispersion layer dimension being $x_S$. Finally, the resonator is completed by the mirror layer M with thickness $x_M$. Since the composite resonator is surrounded by air with a specific acoustic impedance being some order of magnitudes lower than the acoustic impedance of any solid body, the ultimate terminating reflecting planes are the outside planes 11, 12 of the transducer layer and the mirror layer, respectively. Thus, the total length $x_C$ of the composite structure is defined between these terminating planes. In the upper section of FIG. 1 the spatial course of the acoustic particle velocity amplitude V along the longitudinal direction x is plotted. If the dimensions, the specific acoustic impedance of the layers as well as the electrical driving frequency $f_e$ are chosen according to the invention, the maximum amplitudes in the dispersion are, as indicated, much higher than the maximum amplitudes in the other layers. FIG. 1 shows this amplitude relationship only schematically. The quantitative ratio of the maximum amplitude of the standing resonance wave in the dispersion to the maximum amplitude in the transducer is usually higher than indicated in FIG. 1.

Figure 2:
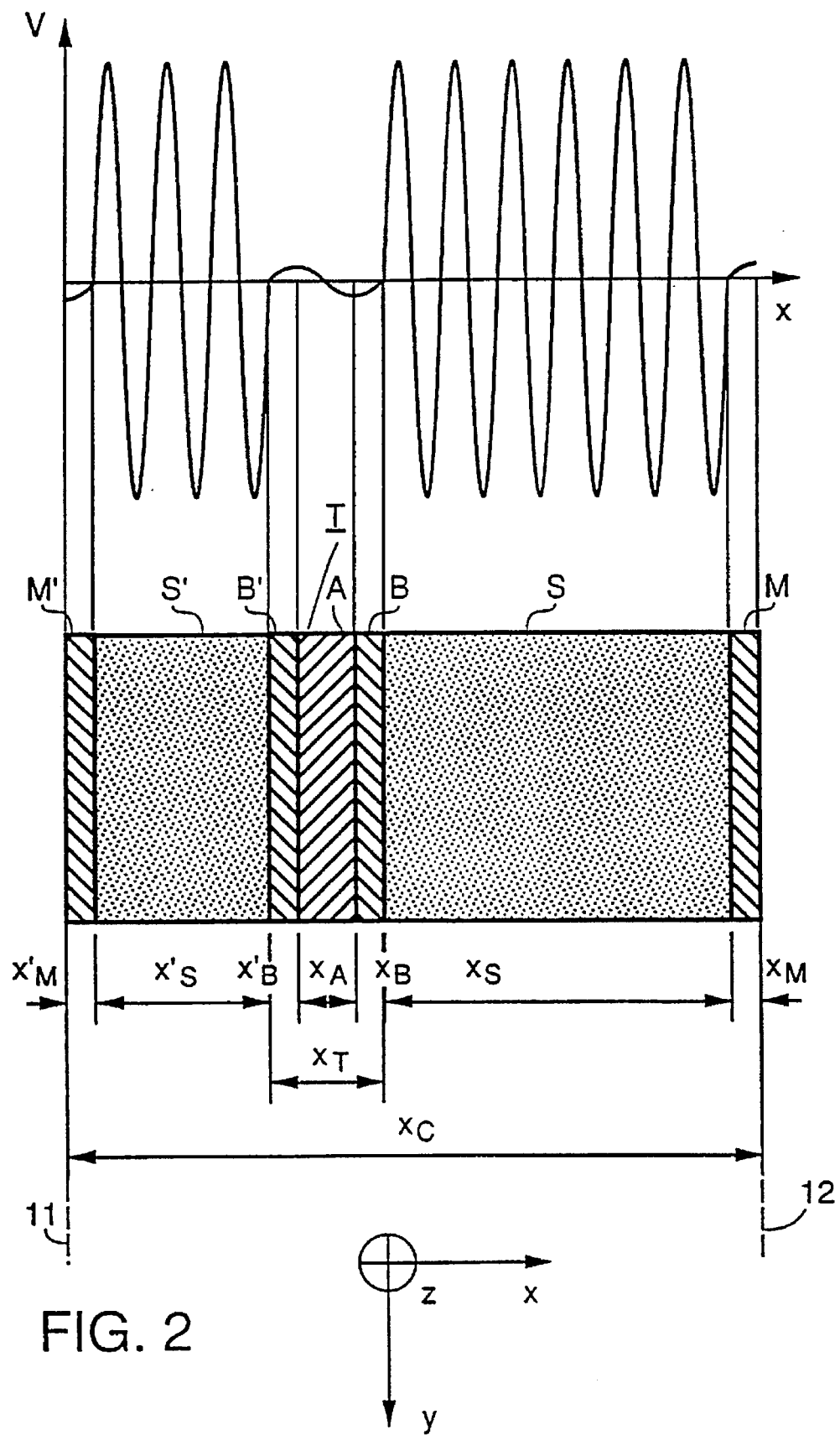
FIG. 2 shows a version of FIG. 1 with the transducer in between two suspension layers.

The section of FIG. 2 shows a schematic of the basic parts and dimensions of a typical one-dimensional piezoelectric composite resonator with the transducer T not only coupled to a first dispersion layer S with the dimension $x_S$ on the right side, but also coupled to a second liquid layer S' with the dimension $x'_S$ on the left side. The second liquid layer S' can either consist of the dispersion or of the dispersion medium (e.g., water) without suspended particles. The transducer layer T preferably consists of an active piezoelectric layer A and two passive, electrically isolating, carrier layers B and B' on both sides of the active layer A. The corresponding layer dimensions are $x_T$, $x_A$, $x_B$, and $x'_B$, respectively. The transducer is acoustically coupled with the dispersion layers S, S', respectively. Finally, the resonator is completed on each side by a first mirror layer M with thickness $x_M$ on the right side, and by a second mirror layer M' with the thickness $x'_M$ on the left side. Since the composite resonator is surrounded by air with a specific acoustic impedance being some orders of magnitude lower than the acoustic impedances of any solid body, the ultimately terminating reflecting planes are the outside planes 11, 12 of the mirror layers M', M, respectively. Thus, the total length $x_C$ of the composite structure is defined between these terminating planes 11, 12. In the upper section of FIG. 2 the spatial course of the acoustic particle velocity amplitude V along the longitudinal direction x is plotted. If the dimensions, the specific acoustic impedance of the layers as well as the exciting frequency $f_e$ are chosen according to the invention, the maximum particle velocity amplitudes in the dispersion layers are, as indicated, much higher than the maximum amplitudes in the other layers.

Figure 3:
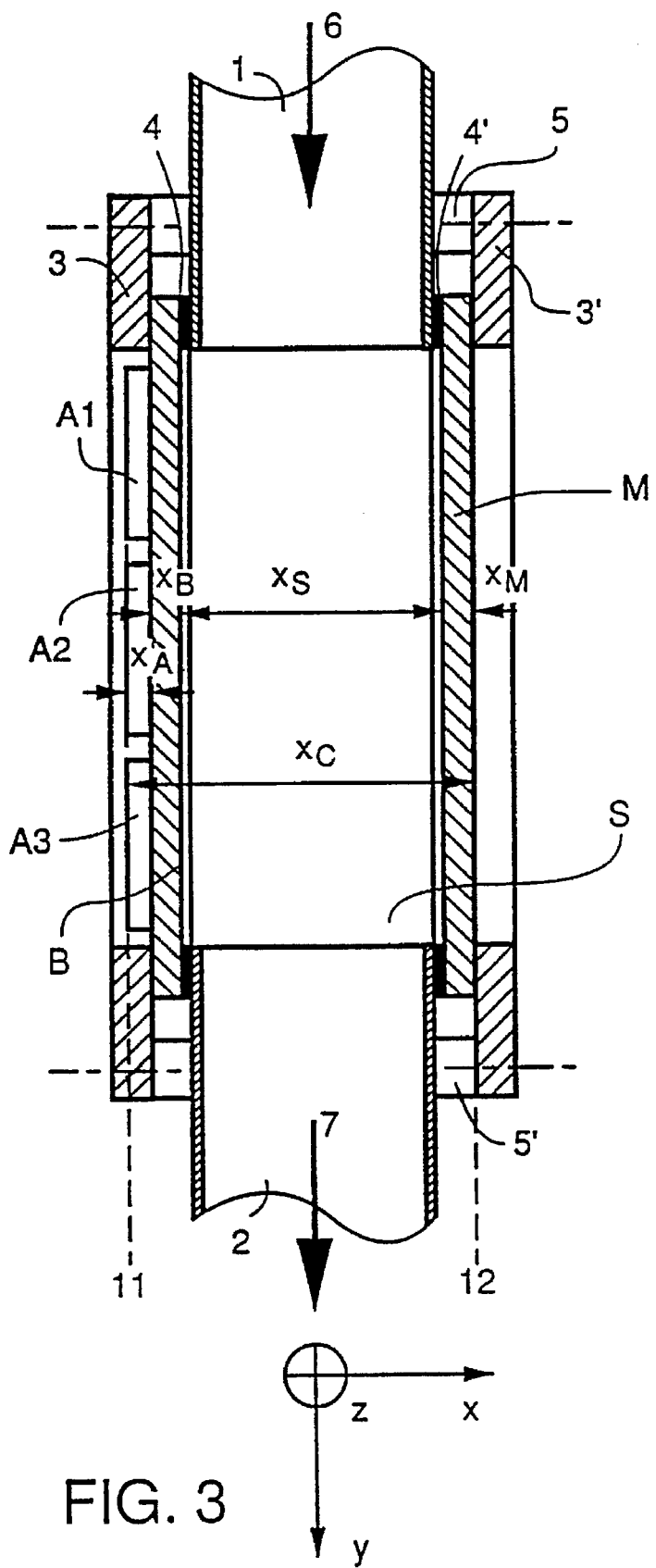
FIG. 3 shows the schematic of a simple resonator example.
Figure 4:
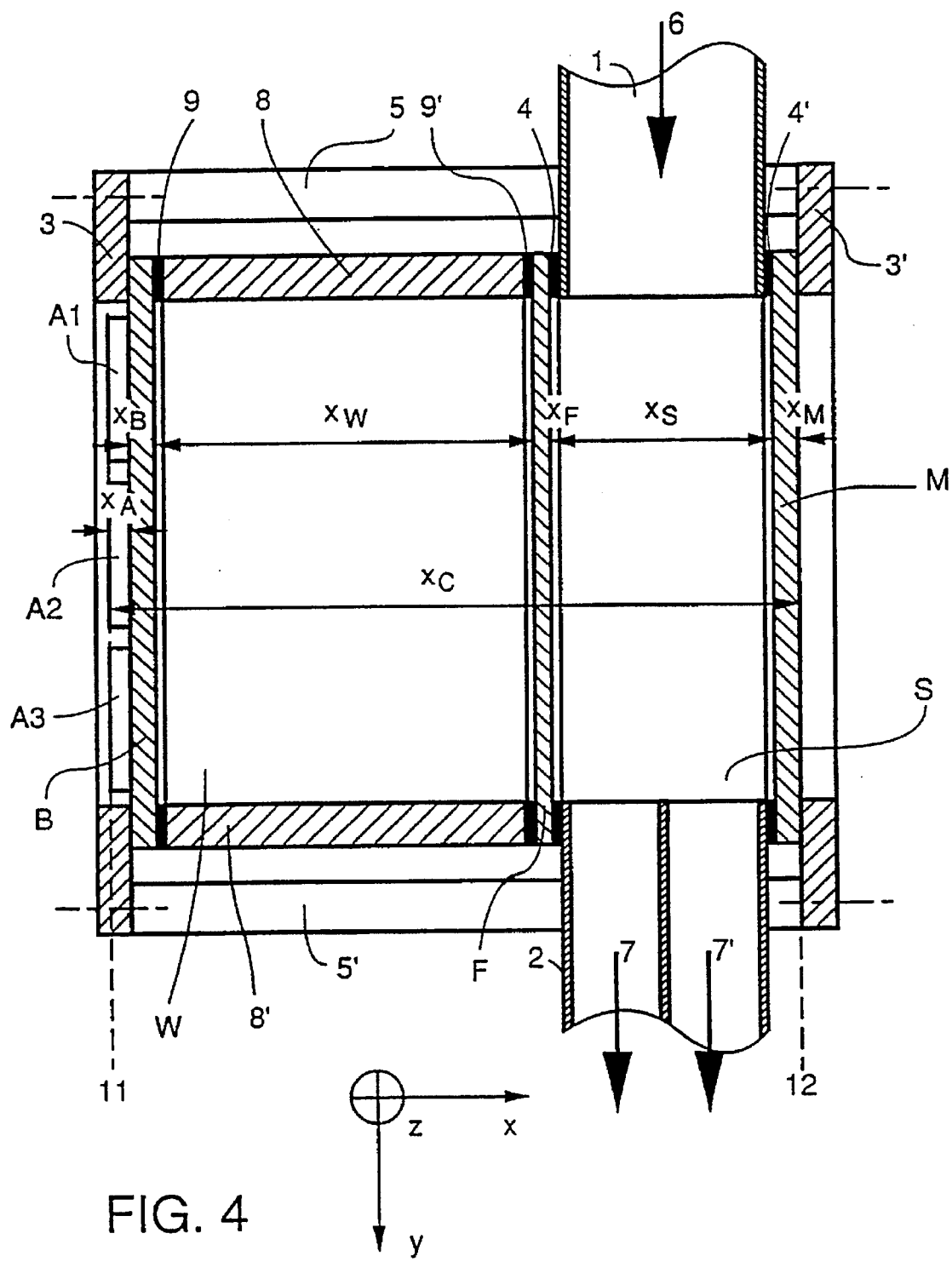
FIG. 4 shows a composite resonator with a wave guide layer.
Figure 8:
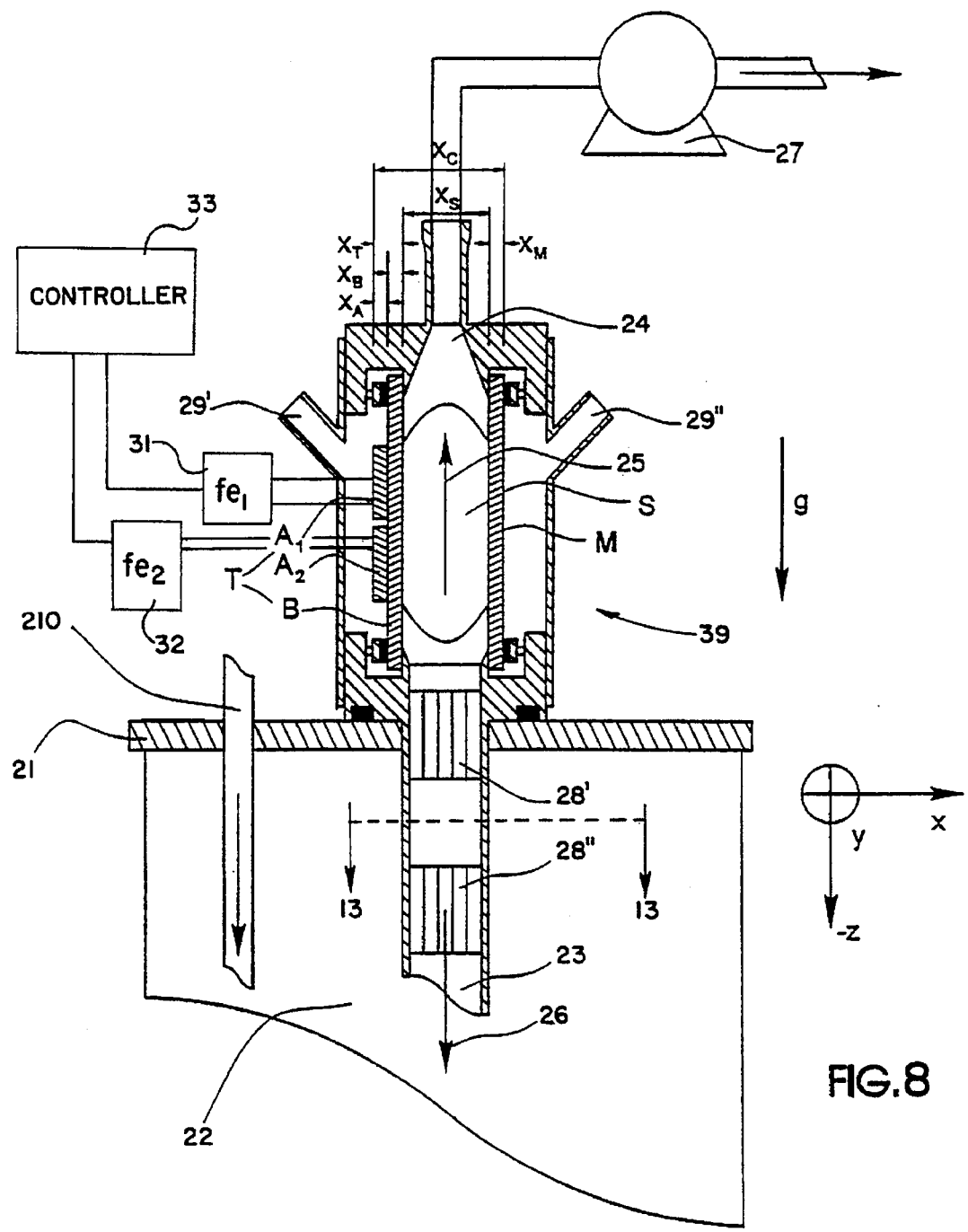
FIG. 8 is a detailed drawing of one form of an apparatus according to one embodiment of the invention.

FIG. 3 shows the schematic of a simple resonator. In this example, the piezoelectric layer is represented in y-direction by three piezoceramic plates or discs A1, A2, A3 of an equal thickness $x_A$, arranged side by side and provided with electrodes. The plates A1, A2, A3 are acoustically working parallel (in phase excited), while they are electrically connected in series. The plates A1, A2, A3 are bonded to a carrier plate B (e.g., glass or $Al_2O_3$-ceramic) with thickness $x_B$ and can be treated in good approximation as one continuous layer A with thickness $x_A$. The flow direction 6, 7 of the dispersion S is in direction y. The dispersed particles are driven by the acoustic radiation forces in longitudinal direction towards the antinode planes of the acoustic particle velocity, where the dispersed particles are agglomerated. The agglomerations are dragged by the gravity forces pointing downwards in direction y (enforced sedimentation by acoustically stimulated coagulation). The carrier plate B and the mirror plate M simultaneously perform as walls of the dispersion vessel. The rectangular cross-sectioned entrance 1 and exit 2 pipes are made tight to the carrier plate B and the mirror plate M via Viton®-rubber stripes 4 and 4', respectively. The distance ($x_B+x_S+x_M$) is precisely determined by the distance-rods 5 and 5' and the flanges 3, 3'. That is, the length of rods 5 and 5' and flanges 3 and 3' are selected to match or provide an exact desired dimension of $x_C$ for the structure as shown in FIGS. 3, 4, and 8.

For example, the preferred dimensioning of two resonators according to the invention is as follows:

For biological cells with diameters of the order of 10 μm the appropriate driving frequency $f_e$ is typically around 2 MHz which is significantly higher than the characteristic frequency from the calculation of equation (I), in order to avoid cavitation. As standard piezoceramic plates are chosen:

| Piezoelectrically active layer A: | |
| --- | --- |
| Material: | PZT Lead-Zirconate-Titanate, Pb(Ti,Zr)O3 piezoceramic Hoechst Sonox P4 |
| Mass Density: | $\rho_A$ = 7800 kg/m³ |
| Effective sound velocity for shortened electrodes: | $v_A$ = 3950 m/s |
| Specific acoustic impedance: | $Z_A$ = 30.8 · 10⁶ kg/m²s |
| Thickness: | $x_A$ = 1 mm |

The fundamental series resonance frequency for layer A can be determined from equation (III): $f_A$=1.97 MHz. The series resonance frequency is relevant, because the driving electronics G is assumed to be of the usual low source impedance type. Six (2×3) square plates with 25 mm×25 mm face dimensions are bonded upon a passive layer B (compare also FIG. 7), the thickness value $x_B$ of this passive layer is chosen equal to a standard glass thickness:

| Piezoelectrically passive layer B: | |
| --- | --- |
| Material: | Tempax glass |
| Mass density: | $\rho_B$ = 2200 kg/m³ |
| Sound velocity: | $v_B$ = 5430 m/s |
| Spec. ac. impedance: | $Z_B$ = 12 · 10⁶ kg/m²s |
| Thickness: | $x_B$ = 2.8 mm |

The resonance frequencies of the two-layer transducer surrounded by environmental air can be measured or calculated (E. Benes, J. Appl. Phys., Vol 56, No. 3, August 1, 1984). The first four quasi-harmonic frequencies are:

$f_{T1}$=573500 Hz,
$f_{T2}$=1371400 Hz,
$f_{T3}$=1958120 Hz,
$f_{T4}$=2546390 Hz.

According to equation (X) the advantageous intervals for the driving frequency $f_e$ are:

0 Hz<$f_e$<516150 Hz; 630850 Hz<$f_e$<1302830 Hz; 1439970 Hz<$f_e$<1892849 Hz; 2023391 Hz<$f_e$<2482730 Hz;
. . .

The dispersion layer dimension $x_S$ depends for instance on the flow rate required and is chosen to be 25 mm:

| Dispersion layer S: | |
| --- | --- |
| Material: | Hydrosol |
| Mass density: | $\rho_S$ = 1000 kg/m³ |
| Sound velocity: | $v_S$ = 1500 m/s |
| Spec. ac. impedance: | $Z_S$ - 1.5 · 10⁶ kg/m²s |
| Thickness: | $x_S$ = 25 mm |
| Mirror layer M: | |
| Material: | Tempax glass |
| Mass density: | $\rho_M$ = 2200 kg/m³ |
| Sound velocity: | $v_M$ = 5430 m/s |
| Spec. ac. impedance: | $Z_M$ = 12 · 106 kg/m²s |
| Thickness: | $x_M$ = 1.3 mm |

These parameters result in resonance frequencies $f_{Cj}$ of the composite resonator with a distance $\Delta f_{Cj}$ of approximately 26 kHz. Therefore, there are many composite resonance frequencies falling into the advantageous intervals. For example, the first resonance frequency $f_{Cj}$ in the fourth interval is 2035555 Hz, the second 2061024 Hz, the third 2087140 Hz; thus, the exciting frequency $f_e$ can be chosen for instance to be equal to 2087140 Hz. Since the fundamental Eigen-frequency of the mirror is 2088460 Hz, the selected driving frequency is not sufficiently mismatched to the mirror resonances, as a consequence, the mirror thickness has to be changed, e.g., to 1.8 mm.

A design which is optimal with respect to the object of the invention uses, except the passive layer B, the same layers. The passive layer B is made of a thickness $x_B$ that produces a node of the particle velocity amplitude V at the interface transducer/dispersion. If the driving frequency $f_e$ is selected to be about the Eigen-frequency $f_A$ of the active layer A, which guarantees optimal excitation of the composite resonator, the phase shift $\phi_A$ in the active layer A is equal to $\pi$. Since there is an antinode boundary condition at the interface plane 11 between active layer A and surrounding air, and since the phase shift $\phi_A$ in the active layer A is equal to $\pi$, the phase shift $\phi_B$ in the passive layer B must be chosen to be equal to $\pi/2$ or equal to an odd multiple of $\pi/2$ to obtain a node of the particle velocity V at the interface plane between transducer T and dispersion S. Introducing this phase shift $\pi/2$ in equation (II) yields $$\phi_B = 2\pi \cdot f_e \cdot x_B / V_B = \pi/2$$

and allows the calculation of $x_B$. If for a more rugged application the result of $x_B = 1.2$ mm is mechanically too weak, three times the value can also be used.

| Piezoelectrically passive layer B: | |
| --- | --- |
| Material: | Alumina (Al$_2$O$_3$) ceramic |
| Mass density: | $\rho_B = 3780$ kg/m$^3$ |
| Sound velocity: | $v_B = 9650$ m/s |
| Specific acoustic impedance: | $Z_B = 36.5 \cdot 10^6$ kg/m$^2$s |
| Thickness: | $x_B = 1.2$ mm |

The first two Eigen-frequencies of this transducer are $f_{T1} = 1335150$ Hz, $f_{T2} = 2866080$ Hz. According to equation (III) the intended driving frequency $f_e = 1.97$ MHz is now approximately in the middle of the advantageous interval: $1468665$ Hz $< f_e < 2722776$ Hz.

In this example the optimum thickness for the mirror is determined from (II):

$$\phi_M = 2\pi \cdot x \cdot f_e / v_M = \pi/2;$$

x=0.692 min. Since this value is rather too small for a reasonable mechanical ruggedness, three times this value is chosen $x_M = 2.07$ mm.

Similar to the composite transducer T, the mirror M may also consist of an active A and a passive B layer with the same criteria for choosing the thicknesses $x_A$ and $x_B$ of such layers, respectively. The active layer of the mirror provides an electric signal, which can be used to automatically control the exciting frequency $f_e$ towards a preferred composite resonance frequency $f_{Cj}$.

FIG. 4 shows an extension of the composite resonator according to FIG. 3. In this example, an additional wave guide layer W, filled with a low loss liquid (e.g., distilled water), separated by an acoustically transparent wall F from the dispersion S, is inserted. The dimension $x_F$ of the wall F is, with respect to the excitation frequency $f_e$, either small compared to a quarter of the wavelength or equal to half-wavelength or a multiple of the half-wavelength in that wall material, or the specific acoustic impedance of the wall material is approximately the same as the specific acoustic impedance of the dispersion. In the first case, e.g., Saran® or Mylar® foils with a thickness of 10 μm are used as wall F. In the second case, the wall F can be made virtually of any material, but for a material with a specific acoustic impedance close to the specific acoustic impedance of the dispersion S, the dimension of the layer F is less critical. Using the phase-nomenclature, the acoustically transparent layer F produces a phase shift $\phi_F$ of an integer multiple of $\pi$. In the third case, a proper material is, e.g., TPX (Methylpestene) or ABS (Acrylonitrite Butadiene Styrene). The additional wave guide layer W serves as a high quality factor resonator part, which removes the very inhomogenous near field region of the transducer T from the separation zone S, thus significantly reducing the potential for acoustic streaming in the dispersion S. This resonator design version allows also an enhanced cooling and a temperature control of the system by circulating a liquid between the wave guide layer W and a thermostat. In this case the side walls 8 and 8' can be equipped with an entrance and exit pipe, respectively. This resonator design version also proofs the applicability of this invention to the so called drifting resonance field (DRF) concept described in a recent patent application (U.S. application Ser. No. 474,813 and PCT Appl. No. PCT/AT89/00098). In the case of the DRF separation procedure, the composite resonator is not only driven at one certain harmonic resonance frequency, but is rather switched repeatedly between, e.g., five to twelve, adjacent, closely spaced resonance quasi-harmonic frequencies $f_{Cj}$. Particles dispersed in the dispersion S are moved in a stepwise manner as a result of movements of the antinode planes in longitudinal direction x. This allows the splitting of the dispersion exit pipe 2 into two parts, one 7 for the clarified dispersion medium, the other 7' for the dispersion medium highly enriched in dispersed particles. To minimize acoustically induced dissipation, the exciting frequencies of the DRF procedure have to be tuned towards resonance frequencies in the neighborhood of preferred resonance frequencies $f_{Cj}$ according to the invention.

Figure 5:
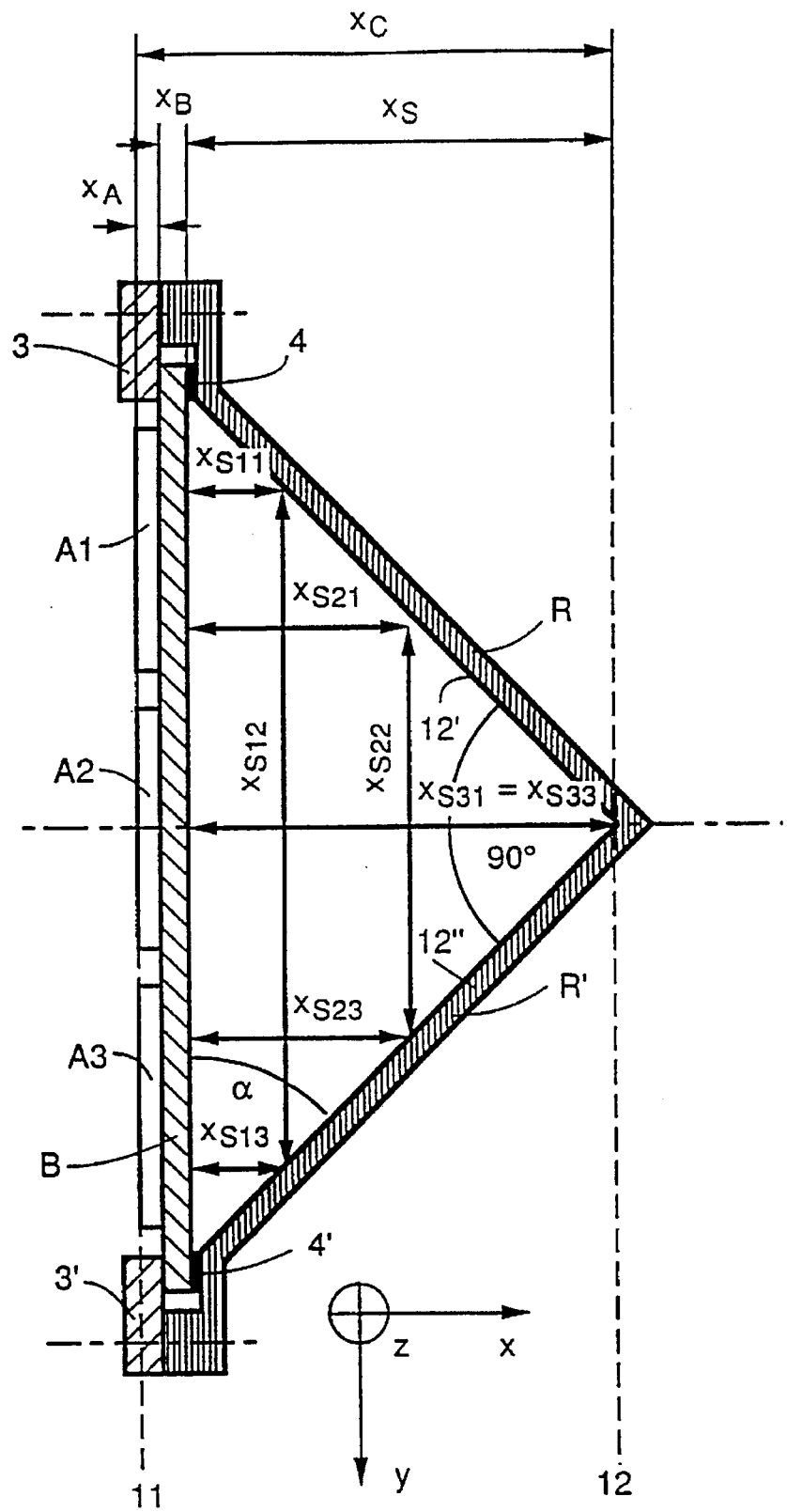
FIG. 5 shows the cross section of a composite resonator using a totally reflecting mirror as resonator termination.

FIG. 5 shows the cross section of a composite resonator using a totally reflecting retro-reflector R as mirror terminating the composite resonator. Said retro-reflector R is preferably formed by two plates at right angle to each other. The orientation of the flow of the dispersion S is preferably chosen opposite to the orientation of the force of gravity and coincides in FIG. 5 with the z-axis. This resonator version is especially advantageous, since there are no side walls engaged which have to be ignored or neglected with respect to their acoustic influence in order to allow a one-dimensional treatment. In contrast to that, a well defined one-dimensional behavior of resonators according to FIG. 3 and FIG. 4 can often only be obtained, if the lateral dimensions of the layers are much higher than the longitudinal ones, which is sometimes not desirable.

The acoustic material parameters of the retro-reflector R must be of a value so that the total reflection condition at the interface between dispersion S and reflector R is fulfilled for the tilt-angle α of the reflector being equal to 45°. Total reflection at the interface-planes 12', 12" between dispersion and retro-reflector disables any acoustically induced dissipation in the reflector R. If the medium of the reflector R is chosen isotropic having a value of the sound speed for shear waves equal to or higher than 1.41 times the sound speed for longitudinal waves in the dispersion S, the limit angle for the total reflection condition at the interface between dispersion S and reflector R is exceeded for the tilt-angle α of the reflector being equal to 45°. On the case the reflector R is made from an anisotropic medium, the lower of the two possible shear-wave sound speeds must be equal to or higher than 1.41 times the sound speed for longitudinal waves in the dispersion S.) That is, the excited sound waves are, for the case of neglected losses within the media, totally reflected already at the interface-planes 12', 12" between dispersion and reflector. This condition is fulfilled, e.g., for an aqueous dispersion and the reflector wall materials Molybdenum, stainless steel and even for the wall material Aluminum. Although the actual sound paths along the distances $x_{S12}$ and $x_{S22}$ are now falling parallel to the y-axis, the total length of any sound path in the dispersion is equal:

$$(x_{S11}+x_{S12}+x_{S13})=(x_{S21}+x_{S22}+x_{S23})=2x_S.$$

Thus, a virtual total reflection plane 12 of an equivalent one-dimensional resonator can be defined, whereby the effective layer thickness $x_S$ of the dispersion S is constant versus lateral directions y and z and all layer dimensions again can be chosen according to the invention.

Figure 6:
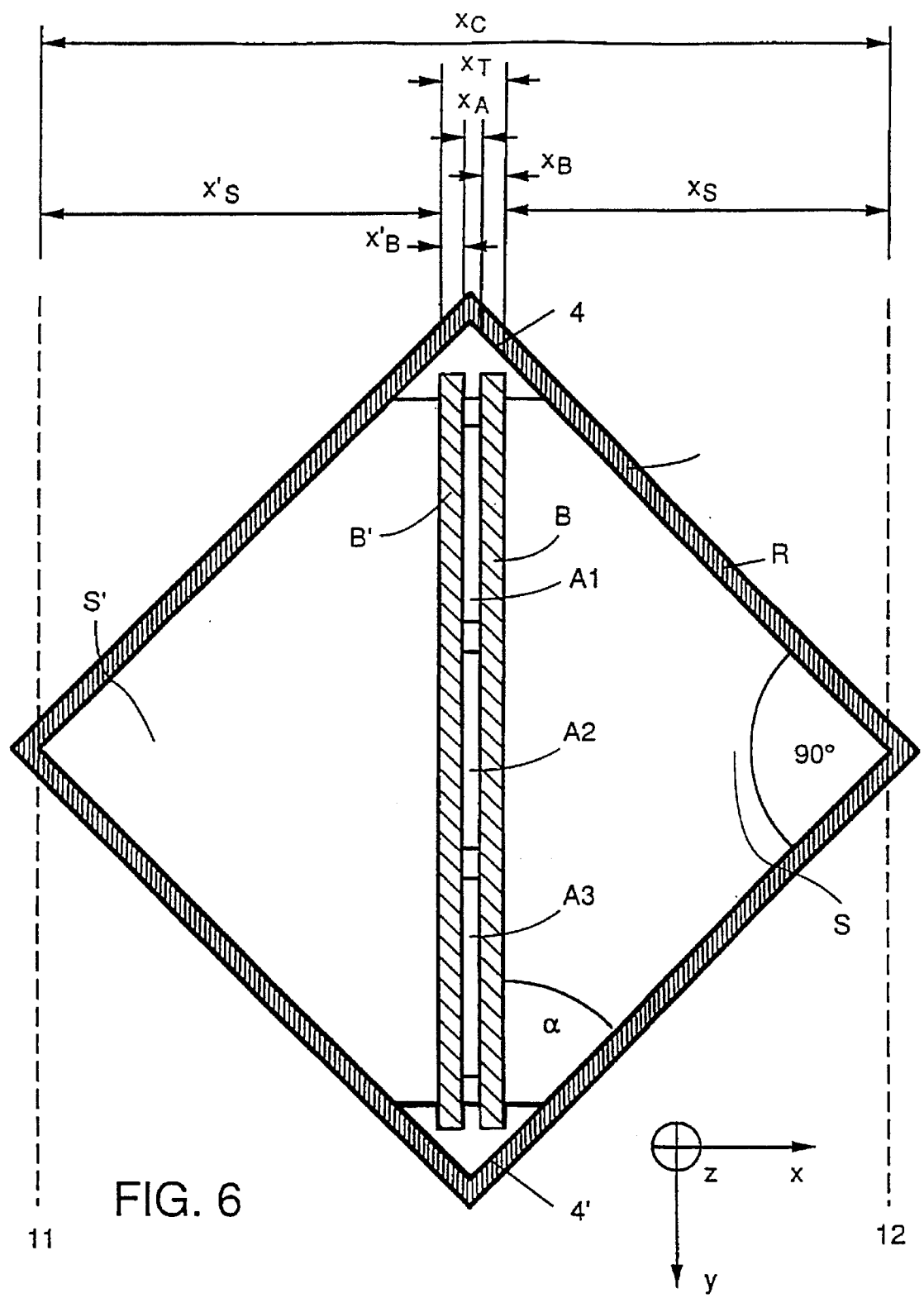
FIG. 6 is a preferred symmetric version of the resonator according to FIG. 5.

FIG. 6 is a preferred symmetric version of the resonator shown in FIG. 5. The main advantage of this design is the use of a square cross section tube, whereby the tube walls simultaneously perform as walls for the dispersion and as totally reflecting means for the composite resonator. Each of the thicknesses $x_B$, $x_B'$ of the two passive layers B, B', as well as the thickness $x_A$ of the active layer A, are chosen according to the invention.

Figure 7:
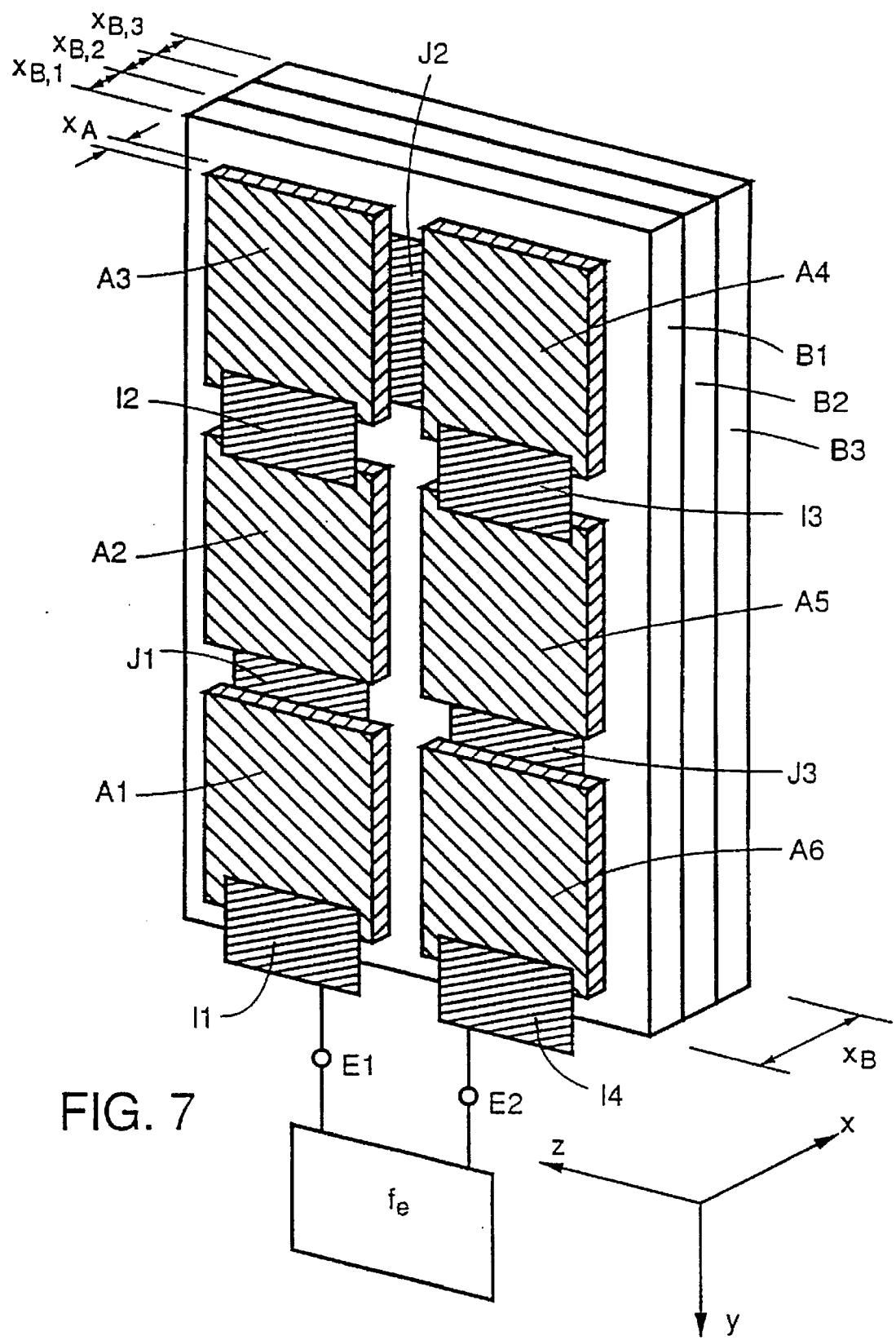
FIG. 7 shows an example of a transducer layer according to one embodiment of the invention.

FIG. 7 shows a more detailed drawing of a composite transducer. The same drawing applies for an active mirror, which includes a piezoelectric layer A according to the invention. In the example shown in FIG. 7, the piezoelectrically active layer A is represented by six piezoelectric plates A1, A2, A3, A4, A5, A6, which are of equal thickness $x_A$, arranged side by side and provided with electrodes. The plates are acoustically working parallel (excited in phase), while they are electrically connected in series to match the electrical impedance of the transducer to the output of the frequency generator G. Said generator G provides via the clamps E1, E2, the electrical excitation signal with a frequency $f_e$. $U_e$ and $I_e$ are the amplitudes of the driving voltage and current, respectively. The plates are bonded upon an electrically insulating and piezoelectrically passive carrier plate B of a thickness $x_B$, such as glass or $Al_2O_3$-ceramic, and can be treated in good approximation as one continuous layer with a thickness $x_A$. The electrical connections between the piezoelectric plates are provided by copper films I1, I2, I3, I4, and by electrode layers J1, J2, J3, of a thickness $x_E$, which causes a phase shift $\phi_E$ of less than 1/16 of the number π. Said electrodes are deposited onto the surface of the passive carrier layer B next to the active layer A. The thicknesses $x_A$ and $x_B$ have defined values according to the invention in order to achieve low acoustically induced thermal dissipation. Best results can be achieved if the specific acoustic impedance $Z_B$ of the passive layer is close to or higher than the specific acoustic impedance of the piezoelectrically active layer $Z_A$. The thickness $x_A$ of the active layer is preferably close to or equal to a value, which causes a phase shift $\phi_A$ being an odd multiple m of the number π, the thickness $x_B$ of the passive layer B is preferably close to or equal to a value, which causes a phase shift $\phi_B$ being an odd multiple n of half of the number π. An odd multiple q of passive sublayers B1, B2, B3, (or more) each of a thickness $x_{B,k}$ (k=1 ... q) causing a phase shift $\phi_{B,k}$ as described above for a single passive layer B is also useful to lower energy dissipation. Said odd multiple of passive layers Bk are of alternating high ($Z_{B,k} \geq Z_A$, k ... odd) and low ($Z_{B,k} < Z_A$, k ... even) specific acoustic impedance, but starting and ending with high ones in the range of $Z_A$ of the active layer A. In a variation of this arrangement of passive sublayers Bk, low-impedance sublayers may also be a fluid.

FIG. 8 shows a structure designed according to the invention and illustrates the inventive method. One possible application for the embodiment described is the separation of medium (containing a desired product) from mammalian cells, which are grown within said medium in a bioreactor 21. A composite transducer layer T, a mirror layer M and a suspension layer S form a multilayered composite resonator with a total length $x_C$. The composite transducer T consists of one or several solid, piezoelectrically active plates with electrodes $A_1$, $A_2$ (or more), of a thickness $x_A$ (together referred to as active layer), and of a dielectric, solid, piezoelectrically passive layer B of a thickness $x_B$. The piezoelectric plates $A_1$, $A_2$ (or more), e.g., PZT (Lead-Zirconate-Titanate) ceramics, are bonded onto the passive layer B which has a specific acoustic impedance $Z_B$ close to the specific acoustic impedance $Z_A$ of the active layer. At the interface of said layers, the passive layer B is coated with thin connecting electrode layers of a thickness $x_e$, which causes a phase shift $\phi_e$ of less than 1/16 of the number π (not shown). Mirror M and passive layer B also form walls of the vessel containing the suspension S.

For FIGS. 8–13, the flow direction of the suspension liquid is generally perpendicular to direction x and parallel to the direction z. Direction y is the depth of resonation chamber and is perpendicular to both directions x and z.

The transducer T is excited by an electric signal of a frequency $f_e$ from power supplies 31 and 32. The operation and timing of power supplies 31 and 32 is controlled by a controller 33. Using two independent power supplies for exciting the active plates A1 and A2 is an option; alternatively, A1 and A2 are driven by a single power source as shown in FIG. 7. The frequency $f_e$ is within the half-value of a longitudinal high-overtone resonance frequency $f_C$ of the composite resonator, whereby, according to the invention, $f_C$ is not in the range of any of the resonance frequencies $f_T$ of the transducer or $f_M$ of the mirror alone. Therefore, the thickness of the transducer $x_T = x_A + x_B$ is close to, or equal to, a value, which causes a phase shift $\phi_T$ being an odd multiple of the number π/2. Also, the thickness of the mirror $x_M$ is close to, or equal to, a value, which causes a phase shift $\phi_M$ being an odd multiple of the number π/2. The specific acoustic impedance $Z_M$ of the mirror is high compared to the specific acoustic impedance $Z_S$ of the suspension.

The resonator is mounted onto the head plate 21 of the bioreactor 22 in vertical position z. According to the present invention, the flow direction 25 of the suspension is transversal to the direction of sound propagation x and is oriented against gravity g, which results in a considerable increase in retention time of suspended particles compared to retention time of the fluid within the resonator. The flow rate is chosen to be higher than the value correlated to a thermally induced increase of spatial phase shift $\Delta\phi_S$ of the acoustic wave of one quarter of π within the suspension. In addition the temperature of the outer surface of the transducer T, the side walls of the vessel and the mirror M can be controlled by circulating air or a dielectric liquid through the pipes 29', 29".

Figure 13:
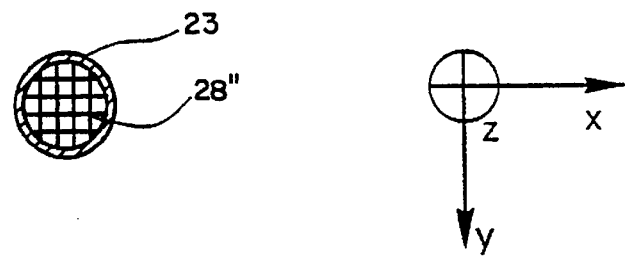
FIG. 13 is a cross-sectional view taken along lines 13—13 of FIG. 8.

The diameter of the inflow tube 23 is approximately equal to the dimension $x_S$ of the square-shaped (x,y) cross section of the suspension layer S. The aggregates tend to stick to any protruding surfaces, therefore the inflow tube 23, being also the settling tube, should be free from protrusions or ledges to which the aggregates may stick and be of a large diameter, preferably approximately equal to or greater than the diameter of the resonation chamber. The big diameter of the inflow tube 3 provides a sufficiently low inflow velocity to allow settling 26 of aggregated particles against flow direction 25. For one embodiment, at least two sets of baffles 28', 28" (or more), decrease turbulence or thermally induced streaming inside the inflow tube 23. The (x,y) cross section of each set is a grid with a grid frequency between 1.5 to 5 cm$^{-1}$ to avoid break up settling aggregates as shown in FIG. 13. The length of one set (along z) typically ranges from 1 to 5 cm, the spacing between two adjacent sets of baffles 28' and 28" is preferably of the same range. If required, a single pass shell and tube heat exchanger (not shown) could replace one set of baffles to precool fluid before entering the resonator. Laminar flow is aided by a cone-shaped outflow port 24, which possibly includes baffles, too (not shown). The pump 27 is placed after the outlet to prevent mechanical damages to recycled cells. Fresh medium is added through pipe 210 to the bioreactor to compensate for harvested medium and allow continuous harvesting. Materials facing the suspension are biocompatible to cell culture, e.g., stainless steel 316, Teflon, borosilicate glass or various ceramics.

Figure 9:
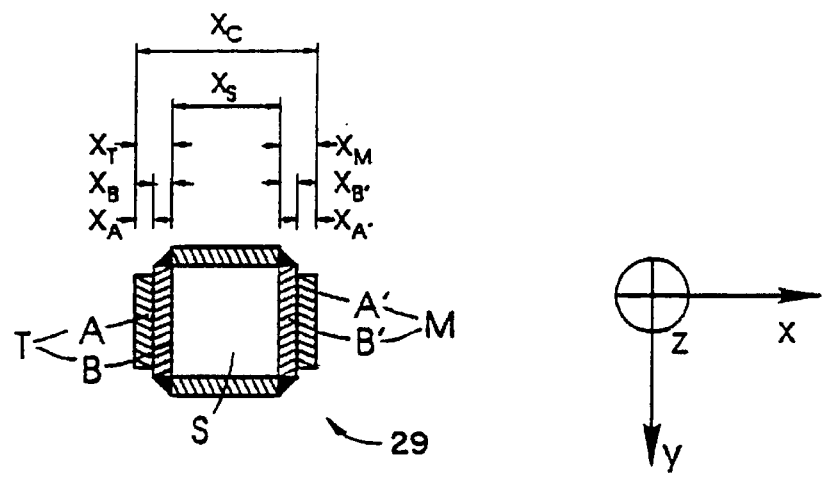
FIG. 9 is a cross-sectional view showing an option of a composite mirror.

FIG. 9 shows the square-shaped (x,y) cross section of the composite resonation chamber 29 of FIG. 8 in which the option of a composite mirror M, is shown. Such a composite mirror consists of a piezoelectrically active layer A', with a thickness $x_A'$, and a piezoelectrically passive layer B', with a thickness $x_B'$, similar to the active layer A and passive layer B of the transducer T. The length of the composite mirror given by $x_M = x_A' + x_B'$ is close to, or equal to, a value, which causes a phase shift $\phi_M$ being an odd multiple of the number $\pi/2$. The active layer of the mirror provides an electric signal, which can be utilized for automatically tuning the exciting frequency $f_e$ toward a preferred composite resonance frequency $f_C$ according to the invention.

Figure 10:
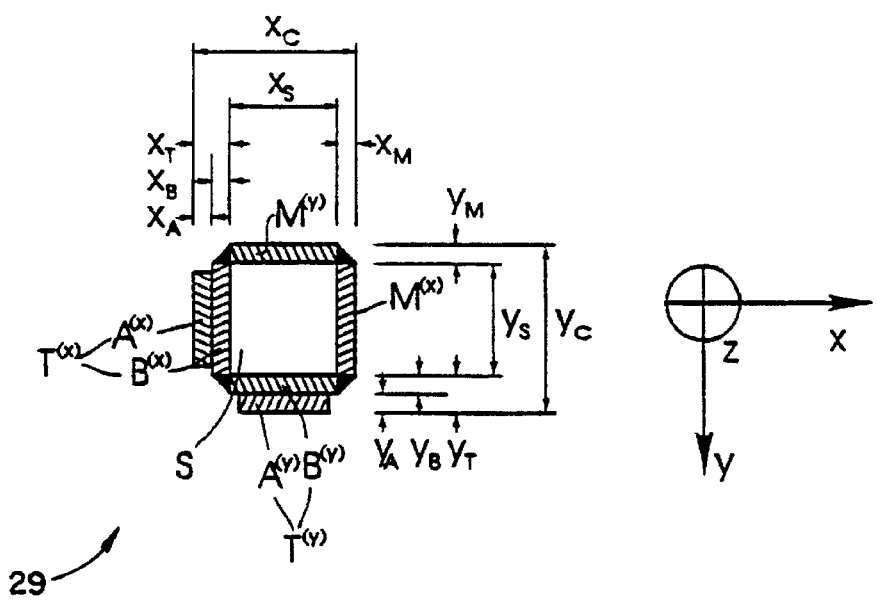
FIG. 10 is a cross-sectional view of a two-dimensional sonication design.

FIG. 10 is a (x,y) cross-sectional view of an alternative design that uses a two-dimensional composite resonation chamber 29 design, whereby the geometry of the one-dimensional multilayered composite resonation 29 is repeated to a second dimension perpendicular to the first one and to flow direction z. The composite resonator in direction x consists of the piezoelectrically active layer $A^{(x)}$ and passive layer $B^{(x)}$ of the transducer $T^{(x)}$, the suspension S, and mirror $M^{(x)}$, whereby the composite resonator in direction y consists of the piezoelectrically active layer $A^{(y)}$ and passive layer $B^{(y)}$ of the transducer $T^{(y)}$, the suspension S, and mirror $M^{(y)}$. All thickness dimensions are chosen according to the invention, as explained herein.

Figure 11:
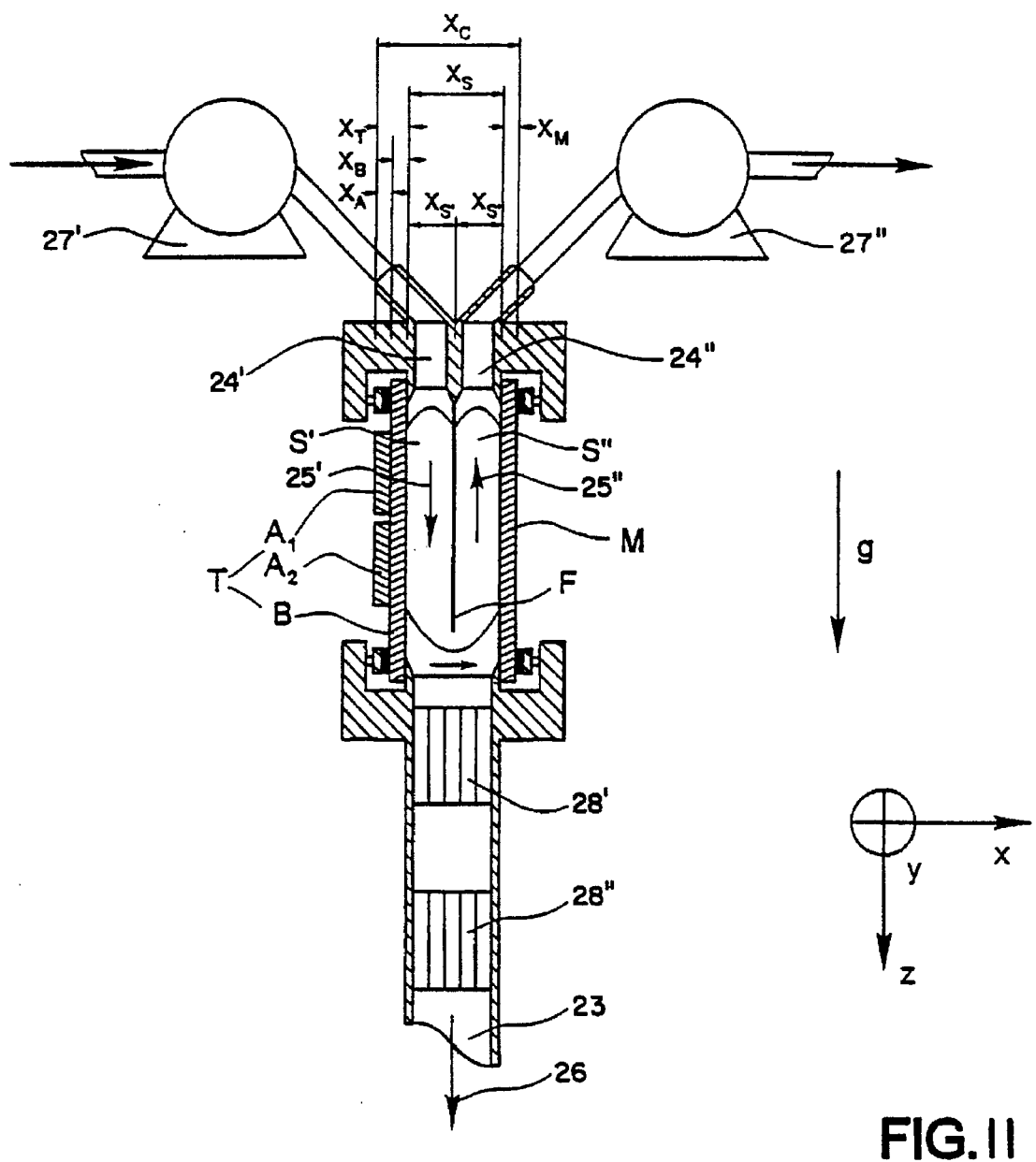
FIG. 11 shows a counter flow in the resonation chamber.
Figure 12:
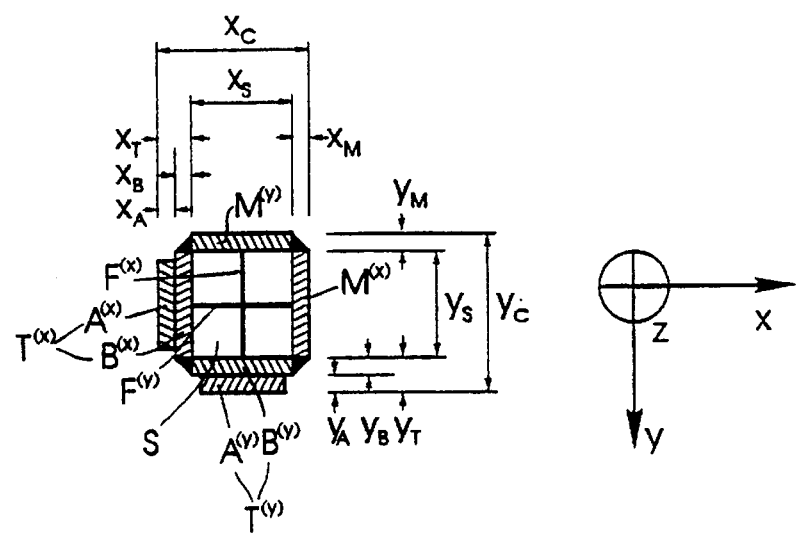
FIG. 12 is a cross-sectional view of an alternative embodiment of a counter-flow resonation chamber.

FIGS. 11 and 12 show a variation of FIG. 8 to compensate for the effect of the spatial temperature gradient versus flow direction. An acoustically transparent layer, referred to as film layer F, divides the suspension layer into a down-flow section S' and an up-flow section S" in transversal orientations z, −z, respectively, perpendicular to the direction of sound propagation x. The acoustic impedance $Z_F$ of said layer F is close or equal to the caustic impedance $Z_S$ of the suspension S', S". The thickness $x_F$ of the layer F can be either small compared to the dimension of a quarter of the wavelength or close to, or equal to, the half-wavelength in that film layer material for the exciting frequency $f_e$ of the power generator driving the transducer. The suspension enters the entrance port 24' of the resonator and passes through the section S' of the chamber next to the transducer T. An outflow pump 27" at the exit port 24" operating at a slightly slower flow rate than the inflow pump 27' at the entrance port 24' results in a low net downward flow within the settling tube 23. Most of the partially clarified media enter and pass through the second section S" of the resonance chamber close to the mirror M, while acoustically aggregated particles settle down 26 the settling tube 23 at the base of the chamber, facilitated by the net downward flow. The counter flow of media on either side of the acoustically transparent layer F results in a uniform average temperature across the entire length of the composite resonator. This compensates for spatial temperature gradients caused by acoustically induced dissipation and allows a uniform resonant field to be maintained despite thermal gradients on either side of the membrane. The higher flow rate next to the transducer T should offset the additional electrically induced thermal dissipation from the transducers as well as higher acoustically induced thermal dissipation within the more concentrated particulate suspension in the down-flow section S' compared to the up-flow section S". The operation of this device can be modified in the following way: the inflow pump 27' can be eliminated and provision made to block the recycle tube 23 at the base of the chamber. The recycling system can then be operated in a semicontinuous fashion with periodic opening of the recycle tube accompanied with back flushing the accumulated particles to a recycling vessel.

FIG. 12 illustrates an alternative embodiment in which two layers F, perpendicular to each other, are used. In the embodiment of FIG. 11, only a single layer F is present, separating the suspension layer into two sections. In the alternative embodiment, the separation layer is segregated into four sections as shown in FIG. 12. According to the modification of FIG. 12, a two-dimensional field as introduced in FIG. 10 is used. In that case, two acoustic transparent layers $F^{(x)}$ and $F^{(y)}$ in perpendicular position to each other are required, dividing the vessel into two up-flow and two down-flow sections. Generally, the suspension layer can be split up in any number of suspension layers parallel to transducer and mirror, as long as counter flow of suspension is provided in adjacent suspension layers.

FIG. 13 is an illustration of the baffle grid 8 as shown in FIGS. 8 and 11. Specifically, the baffle grid has a plurality of walls extending completely across the inlet tube 23. The grid spacing can be in the range of 1.5–5 grids per cm depending upon the size of the inlet tube 23. While a circular inlet tube 23 is shown, the tube could also be rectangular or square.

The operation of the invention according to the embodiments shown in FIGS. 8–13 are as follows. A culture of cells, preferably mammalian cells, are grown in a stirred tank bioreactor chamber 22. The chamber 22 is a stirred chamber using prior art techniques for mixing to ensure that aggregates are properly separated inside the chamber 22, itself. It is desirable to retain viable cells within the bioreactor chamber 22. In biotechnology, these cells can be used to produce proteins or other secreted products of pharmaceutical importance. The products of such cells are secreted into the liquid medium within the bioreactor chamber 22. It is desirable to keep as many viable cells within the bioreactor chamber 22 while at the same time removing the useful byproducts, such as proteins or other secretions which have been produced by the viable cells. Therefore, according to principles of the present invention, the acoustic resonation chamber 39 is positioned above the bioreaction chamber 22 to filter the viable cells. An inflow tube 23 is inserted into the bioreaction chamber and immersed in the liquid in which the cells are cultured and in which the desired byproduct is located. A pump 27 on the down stream side of the acoustic resonation chamber 39 draws liquid medium, containing viable cells and the byproducts of such cells, into the inlet tube 23 and into the acoustic resonation chamber 39. In one embodiment, baffles 28, comprising baffles 28' and 28" are provided within the inlet 23.

As the fluid is drawn through the acoustic resonation chamber 39, one or more transducers T emit acoustic waves into the bioreaction chamber 39. As previously discussed in detail herein, a standing wave is created of a desired frequency that traps the viable cells in the acoustic reaction chamber. The acoustic waves act as a filter to prevent viable cells from exiting at the outlet 24. As the viable cells collect at the nodes of the standing waves, they begin to aggregate. The maximum acoustic particle velocity amplitude within the suspension is maintained at a value that will not result in damage to the viable cells. The preferred frequency $f_C$ of the composite resonator is in the range of 2 to 4 MHz and is selected based on principles previously described.

As the viable cells aggregate, they begin to form clusters within the antinode planes. When the clusters reach a sufficient size, the clusters settle out via the force of gravity and fall against the direction of the fluid flow generated by pump 27. That is, the clusters of cells descend through the baffles 28' and 28" and back into the mixture where they are broken up in the stirred reactor chamber 22 and continue to secrete the desired byproducts. The liquid which exits from the outlet 24 is substantially free of viable cells and yet contains the desired protein and other byproducts which have been produced by the viable cells. The liquid is placed in a separate container and the desired byproducts are removed using techniques well known in the art.

Nutrients and liquid to replace the liquid which has been removed are placed into the bioreactor chamber 22 via inlet tube 210. The present invention thus provides a technique for continuously removing liquid containing byproducts while ensuring that viable cells are filtered from the liquid using a technique which does not damage the viable cells. The viable cells are retained and cultured in the bioreactor chamber 22 for continued production of the byproducts.

As previously discussed and shown in FIG. 8, according to an alternative embodiment of the present invention, the transducer T is composed of two separate active layers A1 and A2. These regarded segments are simply referred to as transducers A1 and A2. The transducer A1 is driven by a first power supply 31 and the transducer A2 is driven by a second power supply 32. In one embodiment, the $f_{e1}$ and $f_{e2}$ are of the same frequency. Alternatively, different frequencies can be used if desired. The controller 33 controls the timing and operation of the power supplies 31 and 32 providing power to the transducers A1 and A2.

According to one mode of operation, the controller 33 controls the power supplies 31 and 32 to operate them simultaneously for the creation of one or more acoustic standing waves which filter out viable cells and permits them to collect for return to the bioreaction chamber 22. According to an alternative mode of operation, the power supplies 31 and 32 are operated simultaneously for a selected period of time. Then, after a certain time of operation, the controller 33 reduces or completely cuts off power to one of the power supplies, either power supply 31 or 32. The other power supply remains in standard operating mode. When one of the power supplies has the power reduced or removed, the standing wave created by the respective transducer A1, or alternatively A2, is significantly reduced or removed. The removal of the acoustic wave generated by one of the transducers has been found advantageous to permit cells which are collecting in clusters within the antinode planes to be released and descend under the force of gravity, until they have descended back into the bioreaction reactor 22. After one of the power supplies is off for a selected period of time, then the power supply is returned to operation at the standard power and the acoustic wave again begins to act as a filter. Then, a short time later, the other power supply significantly reduces or discontinues the power provided to its respective transducer, and the pattern continues.

For example, at the beginning of the operation, both power supplies 31 and 32 may be operating. After a selected period of time, power supply 32 may be turned off and the acoustic waves transmitted by transducer A2 will cease. Power supply 31 remains on at the standard power and the acoustic waves generated by transducer A1 remain within the resonation chamber 39. Cells which have been aggregating in the nodes from the transducer A2 will therefore be released. Those which are heavy enough can now descend back into the bioreactor 22. Any groups of cells which do not descend will be blocked by the acoustic wave generated by transducer A1. After a selected time period, power supply 32 is turned back on and transducer A2 again generates a standing wave. Then, after another selected time, power supply 31 is mined off and the standing wave generated by transistor A1 is removed. The cells which have been collecting at the antinodes of the standing wave created by transducer A1 now begin to descend and return to the medium in reactor 22. After a selected period of time, power supply 31 once again provides power to transducer A1. This pattern may be repeated. Preferably, the transducers A1 and A2 are positioned spaced from each other along the directional flow of the liquid so that the liquid sequentially passes transducer A2 and then passes transducer A1. The controller 33 controls the timing and operation of power supplies 31 and 32 so that the transducers may be operated simultaneously or turned off in alternation. Alternating the mining off of the power to the transducers arranged in this sequence has been found to be a more effective technique for filtering mammalian cells from the moving liquid than certain prior art techniques. Of course, more than two transducers in series can be used and this mode of operation can be used for the horizontal flow of FIGS. 1 and 2. Alternatively, a single transducer or the composite transducer of FIG. 7 can be used.

When power is applied to the transducer, a portion of the energy is converted into heat. Preferably, the heating up of the transducer itself is minimized by circulation of a cooling period through inlet and outlet pipes 29' and 29". As explained in detail herein, the temperature of the liquid directly affects the phase shift of the acoustic waves traveling through such liquid. It is desired to maintain the temperature change of the liquid below a selected level as it passes through the resonation chamber 39. One technique for ensuring that the temperature change within the resonant chamber 39 is kept at a low level is to maintain a relatively high flow rate of the liquid through the resonation chamber. The liquid is thus only within the resonation chamber for a brief period of time and quickly passes out of the outlet port 24. If the liquid flow rate is too high a flow rate, the acoustic waves may not be able to filter as high a percentage of the viable cells from the liquid as would be desired. The flow rate can therefore be reduced to increase the filtering of the viable cells. According to principles of the present invention, if the flow rate is reduced below a certain level, it will be so low that the temperature of the liquid becomes elevated, creating an undesirable phase shift change between the standing wave at the inlet of the resonation chamber and the standing wave at the outlet of the resonation chamber. Preferably, the flow rate is selected such that the phase shift change between the resonation inlet port and the outlet port of the resonation chamber 39 is less than $\pi/2$. In the example given herein, the preferred phase shift change is in the range of or slightly less than π/4. This corresponds to a temperature change of approximately 2° Kelvin from the inlet of the standing wave to the outlet of the standing wave. There is thus a non-homogeneous temperature distribution between the inlet and the outlet, that is, there is a different temperature at the inlet than at the outlet with a temperature gradient therebetween. The non-homogenous temperature distribution is acceptable so long as the temperature change does not exceed a value that will cause the phase shift to be greater than half π and the preferred embodiment will not cause the phase shift to be greater than approximately one quarter of π.

One specific example follows but those of ordinary skill in the art will easily recognize that the principles of this invention may be applied to numerous different systems of different sizes to achieve a good filtering of the viable cells from the liquid medium passing through the resonation chamber 39.

EXAMPLE

An apparatus according to the invention as shown in FIG. 8 was used as an acoustic filter to separate mammalian cells from medium and to recycle the aggregated cells back to a bioreactor. The hybridoma 2E11 cell line used was grown in Dulbecco's Modified Eagle Medium (DMEM) with 5% newborn calf serum.

DIMENSIONS

The thickness $x_A$ of the piezoelectrically active layer (Lead-Zirconate-Titanate ceramic) of the transducer was 1 mm, the thickness $x_B$ of the passive layer (borosilicate glass) 3.3 min. Eigen-frequencies $f_T$ of this composite transducer in air were measured at 2.25 MHz ($\phi_T=4\pi$) and 2.8 MHz ($\phi_T=5\pi$).

A thickness $x_M=2.7$ mm of the mirror layer (borosilicate glass) has been chosen according to the invention. Eigen-frequencies $f_M$ of this single-layered mirror have been calculated from equation (V) and resulted in 2 MHz ($\phi_M=2\pi$) and 3 MHz ($\phi_M=3\pi$).

The transducer-mirror distance was 25 mm. These Dimensions resulted in a spectrum of resonance frequencies $f_C$ of the composite resonator with a distance $\Delta f_C$ of approximately 28 kHz. According to the invention, the exciting frequency $f_e$ was tuned towards a resonance frequency $f_C$ of the composite resonator at about 2.4 to 2.5 MHz in order to avoid excitation of Eigen-frequencies of the transducer or mirror. As a result, the thickness of the transducer corresponded to a phase shift $\phi_T$ of the acoustic wave inside the transducer close to nine times the number π/2; the total thickness of the mirror corresponded to a phase shift of the acoustic wave inside the transducer close to five times the number π/2. The average active power consumption $<P_{e1}>$ was about 3.5 W, the resonator volume was 35 mL. The total length of the flow path within the resonance field was 5.2 cm; the inflow cell concentration was about $5 \cdot 10^6$ cells/mL at a viability of about 91%.

Depending on the flow velocity v, the typical separation efficiencies $e_v$ for viable cells and $e_{nv}$ for non-viable cells have been monitored:

| v[cm/min]  | $e_v$[%] | $e_{nv}$ | ΔT[K] | $\Delta_{\phi S}$ |
|------------|----------|----------|-------|-------------------|
| 0.9 cm/min | 92%      | 84%      | 3.5 K | 0.45 · π          |
| 1.3 cm/min | 95%      | 83%      | 3.0 K | 0.39 · π          |

-continued

| v[cm/min]  | $e_v$[%] | $e_{nv}$ | ΔT[K] | $\Delta_{\phi S}$ |
|------------|----------|----------|-------|-------------------|
| 1.8 cm/min | 98%      | 80%      | 2.0 K | 0.26 · π          |
| 2.5 cm/min | 96%      | 86%      | 1.7 K | 0.22 · π          |
| 3.6 cm/min | 95%      | 87%      | 1.4 K | 0.18 · π          |
| 5.2 cm/min | 94%      | 89%      | 1.0 K | 0.13 · π          |
| 7.3 cm/min | 92%      | 89%      | —     | —                 |

The increase of phase shift $\Delta\phi_S$ along flow path within the suspension is calculated from the measured temperature difference ΔT between inflow and outflow temperature according to equation (VII). According to the invention, no increase of separation efficiency $e_v$ for viable cells has been achieved at flow velocities correlated to an increase of phase shift $\Delta\phi_S$ of more than approximately one quarter of π. Also, a significant difference between the separation efficiencies $e_v$ for viable cells and $e_{nv}$ for non-viable cells have been observed. Generally, typical inflow cell concentrations range from 0.1 to above 25 million cells/mL.

Reviewing the table which contains the examples, it can be seen that the maximum separation efficiency $e_v$ is found for a flow rate in the range of 1.3–2.5 cm per minute. For example, at a flow rate of approximately 1.8 cm per minute, the filter has a separation efficiency of 98 percent for viable cells. For nonviable cells, the separation efficiency is 80 percent and thus permits a larger percentage of the nonviable cells to escape, which is preferred. The temperature change from the inlet of the resonation condition to the outlet of the resonation condition is approximately 2° Kelvin. This results in a phase shift change $\Delta\phi_S$ of approximately π/4, as shown on the chart as being exactly 0.26π. Slightly higher flow rates, for example, 2 cm per minute to 2.5 cm per minute, are also acceptable for providing high filtering efficiencies of viable cells while permitting a nonhomogeneous distribution of the spatial phase shift $\phi_S$ of the acoustic wave within the suspension in the resonator 39. In other embodiments, using differently sized elements, flow rates in the range of or exceeding 8–10 cm/m are used. For different sized elements, the specific flow rates may vary.

Alternative parameters for the geometry of a multilayered resonator according to the invention are, for example:

The thickness $x_A$ of the piezoelectrically active layer (Lead-Zirconate-Titanate ceramic) of the transducer is 1 mm, the thickness of $x_B$ of the passive layer (Alumina ($Al_2O_3$)-ceramic) 3 mm. This example is especially advantageous, since the specific acoustic impedance $Z_B$ of Alumina-ceramic is higher than the specific acoustic impedance of the piezoelectric active layer $Z_A$. Eigen-frequencies $f_T$ of this composite transducer in air can be measured at 1.8 MHz ($\phi_T=2\pi$) and 2.7 MHz ($\phi_T=3\pi$). Therefore, according to the invention, the exciting frequency $f_e$ has to be chosen within the half-value bandwidth of a resonance frequency $f_C$ of the composite resonator around 2.25 MHz. To optimize mismatching between this exciting frequency $f_e$ and any of the Eigen-frequencies of the mirror according to equation (V), the thickness $x_M$ of the mirror layer (borosilicate glass) has to be chosen at 0.6 mm or any of its odd multiple.

To summarize the basic features of one embodiment of the present invention, an apparatus for separating suspended particles from a liquid by means of applying a resonant ultrasonic sound field in a multilayered composite resonator has been described. Preferably, the composite resonator includes acoustically coupled, parallel layers formed in the longitudinal propagation direction x of the acoustic wave including at least a piezoelectric transducer and an acoustic mirror with the suspension liquid in between them from which the particles are to be filtered. The transducer layer is excited by an electrical power generator with a high frequency ($f_e$) within the range of the half-value bandwidth of a characteristic high overtone resonance frequency ($f_C$) of the multilayered composite resonator 39. Preferably, the thickness ($x_T$) of the transducer is of a value which causes a spatial phase shift $\phi_T$ of the acoustic particle velocity amplitude at the generating frequency ($f_e$) such that the phase shift is close to or equal to an odd multiple of $\pi/2$. The flow velocity of the suspension liquid in the resonation chamber 39 is of a value that results in a temperature distribution ($T_z$) in a direction z, averaged across the resonation chamber in direction x, such that the temperature distribution ($T_z$) causes a nonhomogeneous distribution ($\phi_{Sz}$) of spatial phase shift of the acoustic wave within the suspension liquid having a total range ($\Delta\phi_s$) of less than one quarter of $\pi$. In some embodiments, a total phase shift range in the range from 0 to $\pi/2$ is permissible, however, preferably the phase shift change is in the range of approximately $\pi/4$ or lower.

According to one embodiment, the transducer is comprised of a piezoelectric solid layer with electrodes, referred to as the active layer, and a non-piezoelectric solid layer, referred to as the passive layer whereby the passive layer is made of a dielectric material with a specific acoustic impedance ($z_B$) close to, or higher than the specific acoustic impedance ($z_A$) of the active layer. Alternatively, any other transducer or transducer layer of the type used in the prior art may be used.

In addition, a mirror is provided on the opposite side of the resonation chamber 39 that is made of a material with a specific acoustic impedance ($z_M$) high compared to the specific acoustic impedance ($z_S$) of the suspension liquid and the thickness ($\phi_M$) of the mirror is selected to be of a value which causes a spatial phase shift ($\phi_M$) of the acoustic particle velocity amplitude that is close to, or equal to, an odd multiple of the number $\pi/2$.

Preferably, the flow orientation z of the suspension liquid is oriented against the force of gravity acting in orientation minus z.

According to an alternative embodiment, the piezoelectrically active layer of the transducer is formed by at least two adjacent piezoelectric plates, each plate being bonded onto a single passive layer. Each regarded transducer segment is excited by an individual electrical power generator 31 and 32, and, thus, individual resonant standing waves within the composite resonator 39 are created. The individual periods of excitation are possibly interrupted by individual periods of no excitation resulting in settling periods of the aggregates of cells within the regarded part of the suspension liquid.

In one alternative embodiment, at least one of the individual standing waves is in a direction x and another wave is superimposed by an additional transducer creating an additional resonant standing wave in direction y perpendicular to x, the additional standing wave created by an additional transducer and mirror, which are parallel to each other and are positioned on the side walls of the resonation chamber 39 other than the side walls for the transducer which creates the standing waves in direction x. The direction y of the additional standing wave is perpendicular to the flow direction.

Preferably, the pump which controls the flow rate to the resonation chamber 39 is positioned at the exit pipe only and the entrance pipe is directly connected to the reaction chamber 22, which contains the suspension liquid from which the cells are to be separated.

Preferably, the inner dimensions of the circular, or alternatively rectangular, shaped entrance tube are close to, or equal to, the inner dimensions of the preferably square-shaped cross section of the vessel for the resonation chamber 39. The entrance tube is also the settling tube of the separated particles. In one embodiment, at least two sets of baffles are arranged inside the settling tube 23. The cross section of the baffles, perpendicular to the flow direction, of such a set is grid shaped, the grid frequency being in the range of 1.5–5 grids per cm in one embodiment. The length, and the flow direction, of each set is in the range of 1–5 cm and the space in between two adjacent baffles is in the range of 1–5 cm.

According to a further alternative embodiment, the suspension liquid within the resonation chamber 39 is divided into at least two sections, referred to as suspension sections $S_i$ ($i=1 \ldots k$, $k \geqq 2$) by at least one separation layer F essentially perpendicular to the direction x of the standing wave, referred to as the film layer, f. The film layer F preferably consists of a material with a specific acoustic impedance ($Z_F$) close to the specific acoustic impedance ($Z_S$) of the suspension. The thickness ($x_F$) of the film layer being either small compared to the dimension of a quarter of the wavelength or close to, or equal to, the half-wavelength for the exciting frequency ($f_e$). The suspension flow direction is in a downward direction on one side of the film F and in an upward direction, against gravity on the other side of the film F, resulting in temperature distributions ($T_{iz}$) in the regarded sections $S_i$, such temperature distributions ($T_{iz}$) resulting in said temperature distribution ($T_z$) in direction z, averaged in direction x across all the suspension sections $S_i$. That is, the temperature is averaged in a direction x across the liquid on both sides of the film layer F. Alternatively, two or more film layers F can be used, both parallel to each other and creating a serpentine path for the liquid from the chamber 22 to outlet port 24. For example, the fluid may travel upward for the first one-third of the resonation chamber 39, downward in the middle region of the resonation chamber 39, and upward in the final region.

Preferably, the suspension liquid includes biological cells suspended in a liquid which contains desired products, and the maximum acoustic particle velocity amplitude within the suspension liquid is selected at a value which does not result in damage to the viable biological cells. Preferably, the composite reactor 39 is mounted on a bioreactor growing mammalian cells suspended in a nutrient solution, which may contain desired products. The solution is separated from the viable cells within the resonator 39, the solution being harvested after the exit pipe 24 from the resonator 39, with the viable cells being recycled by descending through the settling tube 23 and back into the bioreactor tube 22. Preferably, only materials biocompatible to such a cell culture are in contact with the suspension liquid.

Preferably, the flow velocity of the suspension liquid through the suspension chamber 39 is selected to be of a value which results in a separation significantly higher for viable cells than for non-viable cells. Thus, an increase in the viability of separated cells is achieved. Separation efficiency is defined as the ratio of the number of cells being separated by the liquid by acoustically induced aggregation and sedimentation to the number of cells entering the resonator within the same time period. Viability is defined as the fraction of viable cells compared to the total number of cells.

While several specific embodiments have been described, the invention and claims are not limited in scope to these specific embodiments. Rather, equivalent structures and methods can be used that incorporate the inventive concepts of various structures. The features of the various embodiments may also be combined in many different ways to practice the invention. The embodiment of FIGS. 8–13 need not be used, are not required to use the transducer structure of FIGS. 1–7 that is designed to avoid excitation of Eigenfrequencies of the transducer, but could use the transducer structures of the prior art if desired.

We claim:

1. A method of separating particles from a liquid comprising:

generating an acoustic standing wave in an acoustic resonation chamber; and drawing the liquid containing the particles through the acoustic resonation chamber at a selected flow rate, the flow rate of liquid through the acoustic resonation chamber being a value selected such that the phase shift change in acoustic standing wave in the liquid is less than one-half of $\pi$ due to a temperature change in the liquid within the resonation chamber.

2. The method according to 1, further including:

drawing the liquid from a bioreactor in which mammalian cells are cultured;

drawing the liquid through two set of baffles prior to passing it through the acoustic resonation chamber.

3. The method according to the claim 1, further including:

generating at least two acoustic standing waves in said resonation chamber using at least two separate piezoelectric layers;

powering the at least two piezoelectric layers simultaneously for a first selected time period;

shutting off power to at least one of the piezoelectric layers while maintaining power to at least one of the piezoelectric layers for a second selected time period after the first selected time period; and powering the at least two piezoelectric layers at a third time period after said second time period.

4. The method according to claim 3 wherein two acoustic transducers are provided that form adjacent walls of a rectangular resonation chamber such that the acoustic waves generated by them are perpendicular to each other.

5. The method of claim 1 wherein a second piezoelectric layer of said at least two piezoelectric layer is spaced laterally from a first piezoelectric layer of said at least two piezoelectric layer in the direction of flow of the liquid such that the liquid sequentially passes said first piezoelectric layer and then said second piezoelectric layer.

6. The method of claim 5, further including:

controlling the generation of the at least two acoustic standing waves by a control means that selectively powers said first piezoelectric layer by a first power generator to generate a first acoustic standing wave, and selectively powers said second piezoelectric layer by a second power generator to generate a second acoustic standing wave.

7. The method of claim 1 wherein said acoustic resonation chamber has an inlet and an outlet, the liquid flowing in said inlet, through said acoustic resonation chamber and exiting at said outlet, and wherein said acoustic resonation chamber has an acoustic transducer and an acoustic mirror that form opposite sidewalls of said resonation chamber and are positioned parallel to each other to generate said acoustic standing wave.

8. The method of claim 7, further including:

generating a second acoustic standing wave in said resonation chamber using a second piezoelectric layer; said second piezoelectric layer having a second acoustic transducer and a second acoustic mirror forming opposite sidewalls of said acoustic resonation chamber and positioned parallel to each other, said second acoustic standing wave being perpendicular to said first acoustic standing wave.

9. The method of claim 8 wherein the direction of the second acoustic standing wave generated by said second acoustic transducer is perpendicular to the flow direction of the liquid.

10. The method of claim 8 wherein said second acoustic transducer is positioned for generating acoustic standing waves that are parallel to the flow direction of the liquid.

11. The method of claim 7, further including:

drawing the liquid through a bioreactor chamber, said bioreactor chamber being positioned prior to said inlet to said acoustic resonation chamber; said bioreactor chamber having an entrance tube with inner dimensions that are substantially equal to the inner dimensions of said acoustic resonation chamber and the liquid containing viable biological cells.

12. The method of claim 11 wherein said entrance tube includes a first set of baffles arranged inside the entrance tube, the cross-sectional shape of the baffles being a grid shape that is perpendicular to the flow direction of the liquid.

13. The method of claim 12 wherein said entrance tube further includes a second set of baffles positioned within the entrance tube and spaced from said first set of baffles along the direction of flow of the liquid such that the liquid passes sequentially through said first set of baffles and said second set of baffles.

14. The method of claim 7, further including:

drawing the liquid through said outlet with a liquid pump at said selected flow rate, said liquid pump being positioned in the flow of the liquid after said acoustic resonation chamber.

15. The method of claim 7 wherein said acoustic resonation chamber further includes a film layer to divide said acoustic resonation chamber into two sections, a first section having a first liquid flow direction and a second section having a second liquid flow direction in opposite flow direction from said first liquid flow direction and further including the steps of:

flowing the liquid in a first direction in the first section; and flowing the liquid in a second, opposite direction passing a second wave simultaneously through the first and second sections while liquid is flowing therethrough.

16. The method according to claim 1 wherein the flow rate of the liquid through the acoustic resonation chamber is a value selected such that the distribution of the spatial phase shift in said acoustic standing wave in the liquid has a total range of less than one third of $\pi$ within said acoustic resonation chamber.

17. The method according to claim 1 wherein the flow rate of the liquid through said acoustic resonation chamber is a value selected such that the distribution of the spatial phase shift in said acoustic standing wave in the liquid is in the range of one quarter of $\pi$ within said acoustic resonation chamber.

18. The method of claim 1 wherein the step of drawing the liquid through the acoustic resonation chamber is carried out by drawing the liquid in a direction against the force of gravity such that the flow direction of the liquid in said acoustic resonation chamber is oriented against the force of gravity.

19. The method of claim 1 wherein the particles are biological cells suspended in a liquid in a bioreactor chamber, which are producing a desired protein product and secreting said desired protein product into the liquid and further including the step of:

removing the liquid containing the secreted protein product from the bioreactor chamber for separation of the protein product from the liquid, said biological cells being returned to said bioreactor chamber by being aggregated in said acoustic resonation chamber and settling against the direction of the flow of liquid into said resonation chamber.

20. The method according to claim 19, further including:

breaking the biological cells that were aggregated after they have settled out of the resonation chamber.

21. A method of separating particles from a liquid comprising the steps of:

generating an acoustic standing wave in an acoustic resonation chamber between an acoustic transducer and an acoustic mirror, said acoustic resonation chamber having an inlet and an outlet, said acoustic transducer and said acoustic mirror being positioned parallel to each other and forming opposite sidewalls of said acoustic resonation chamber; and drawing the liquid through said acoustic resonation chamber from said inlet to said outlet at a selected flow rate, said flow rate being selected to be a rate such that a spatial phase shift of said acoustic standing wave of more than one half of $\pi$ does not occur due to a change in the temperature of the liquid from said inlet to said outlet.

22. The method of claim 21 wherein the flow direction of the liquid in the acoustic resonation chamber is oriented against the force of gravity.

23. The method of claim 21 in which the difference in the liquid temperature is less than 3.5° K. at the outlet from that at the inlet.

24. The method of claim 21 wherein said acoustic resonation chamber has a film layer to divide the acoustic resonation chamber into two sections, a first section having a first liquid flow direction and a second section having a second liquid flow direction essentially in opposite flow direction from the first liquid flow direction with the flow velocities of the two layers resulting in a temperature distribution parallel to the direction of flow, averaged in a direction parallel to the acoustic resonance wave such that the average temperature of both flow layers has a temperature change value so that the acoustic wave does not have a phase shift change greater than one half of x caused by change in the liquid's temperature parallel to the direction of flow.

25. A method for separating biological cell particles from a liquid comprising the steps of:

generating an acoustic standing wave in an acoustic resonation chamber;

drawing the liquid from a bioreactor chamber with a liquid pump through an exit pipe;

drawing the liquid out of the exit pipe and into the acoustic resonation chamber; and drawing the liquid through the acoustic resonation chamber at a flow rate selected such that the phase shift change in the acoustic standing wave in the liquid is less than one half of $\pi$ from said inlet to said outlet and the temperature of the liquid at the outlet is within 3.5° K. of the temperature of the liquid at the inlet.

26. The method of claim 25 wherein the biological cells are producing a desired protein product and secreting said protein product into the liquid.

27. The method of claim 26, further comprising:

aggregating the biological cells within said acoustic resonation chamber;

removing the liquid containing the protein product with said liquid pump for separation of said protein product from the liquid;

recycling the biological cells to said bioreactor chamber by allowing the biological cells to settle by the force of gravity against the direction of flow of the liquid back to the bioreactor chamber;

breaking up the aggregated biological cells after they re-enter said bioreactor chamber.

* * * * *

UNITED STATES PATENT AND TRADEMARK OFFICE
CERTIFICATE OF CORRECTION

PATENT NO. : 5,626,767
DATED : May 6, 1997
INVENTOR(S) : Felix Trampler et al.

It is certified that error appears in the above-identified patent and that said Letters Patent is hereby corrected as shown below:

In column 32, claim 24, line 7, please delete "x" and insert therefor --$\pi$--.

Signed and Sealed this

Twenty-fifth Day of November, 1997

Attest:

BRUCE LEHMAN

*Attesting Officer*   *Commissioner of Patents and Trademarks*